US005641497A

United States Patent [19]

Bevins et al.

[11] Patent Number: 5,641,497

[45] Date of Patent: Jun. 24, 1997

[54] GASTROINTESTINAL DEFENSINS, CDNA SEQUENCES AND METHOD FOR THE PRODUCTION AND USE THEREOF

[75] Inventors: Charles L. Bevins, Drexel Hill, Pa.; Douglas E. Jones, Winslow, N.J.

[73] Assignee: Children's Hospital Of Philadelphia, Philadelphia, Pa.

[21] Appl. No.: 158,189

[22] Filed: Nov. 24, 1993

Related U.S. Application Data

[63] Continuation of Ser. No. 888,232, May 22, 1992.

[51] Int. Cl.$^6$ .......................... A01N 25/00; C07H 21/04; C07K 14/435; C12N 15/63

[52] U.S. Cl. .................. 424/405; 435/172.3; 435/252.3; 435/320.1; 536/23.5; 530/324; 530/350; 424/94.6; 514/12; 514/16

[58] Field of Search .................................... 530/324, 350; 435/320.1, 252.3, 172.3, 69.1; 424/405, 94.6; 536/23.5; 514/12, 16

[56] References Cited

U.S. PATENT DOCUMENTS 4,677,063 6/1987 Mark ........................................ 435/68

FOREIGN PATENT DOCUMENTS

WO90/11734 4/1990 WIPO .

OTHER PUBLICATIONS

Mars et al Blood (1988) 71:1713–1719.
Moore et al J. Biol Chem (Oct. 1991) 266: 19851–19857.
Ouellette et al J Biol Chem (Jun. 1990) 265:9831–9837. Fast DB sequence comparison.
Ouellette, et al., *Febs Letters* 304: 146–148 (1992).
Selsted, et al., *Journal of Cell Biology* 118: 929–936 (1992).
Bateman et al., *J Biol Chem* 266: 7524–7530 (1991).
Behnke and Moe, *J Cell Biol* 22: 633–652 (1964).
Bevins and Zasloff, *Ann Rev. Biochem* 59: 395–414 (1990).
Bohlmann and Apel, *Mol Gen Genetics* 207: 446–454 (1987).
Bohlmann et al., *EMBO J* 7: 1559–1565 (1988).
Bolivar et al., *Gene* 2: 95–113 (1977).
Boman, *Cell* 65: 205–207 (1991).
Boman & Hultmark, *Ann Rev Microbiol* 41: 103–126 (1987).
Borenstein et al., *Infect Immun* 59: 1359–1367 (1991).
Broach, J. et al., *Gene* 8: 121–133 (1979).
Broach, J.R., *Meth Enz* 101: 307–325 (1983).
Chamberlain et al., *Nucleic Acids Research* 16: 11141–11156 (1988).
Chamberlain et al., *PCR Protocols: A Guide to Methods and Applications* (Academic Press, Orlando, FL) 272–281 (1990).
Chen et al., *Science* 238: 263–366 (1987).
Clarke, L. et al., *Meth Enz* 101: 300–307 (1983).
Clewell, D.B., et al., *Proc Natl Acad Sci USA* 62: 1159–1166 (1969).
Clewell, D.B., *J Bacteriol* 110: 667–676 (1972).
Cohen, S., *Proc Natl Acad Sci USA* 69: 2110–2114 (1972).
Cotton et al., *Proc Natl Acad Sci USA* 85: 4397–4401 (1988).
Cowan et al., *Mol Cell Biol* 3: 1738–1745 (1983).
Daher et al., *J. Virol* 60: 1068–1074 (1986).
Daher et al., *Proc Natl Acad Sci USA* 85: 7327–7331 (1988).

(List continued on next page.)

*Primary Examiner*—W. Gary Jones
*Assistant Examiner*—Carla Myers
*Attorney, Agent, or Firm*—Woodcock Washburn Kurtz Mackiewicz & Norris

[57] ABSTRACT

This invention provides gastrointestinal peptides useful as antimicrobial and anti-inflammatory agents. This invention also provides methods for producing peptides, pharmaceutical compositions containing the gastrointestinal defensin peptides, and methods of use thereof. Methods of diagnosing gastrointestinal disorders are also provided.

8 Claims, 11 Drawing Sheets

OTHER PUBLICATIONS

Deckx et al., *Biochim Biophys Acta* 139: 204–207 (1967).
Devereux et al., *Nucl Acids Res* 12: 387–395 (1984).
Diamond et al., *Proc Natl Acad Sci USA* 88: 3952–3956 (1991).
Eisenhauer et al., *Immun* 57: 2021–2027 (1989)*.
Erlandsen et al., *J Histochem Cytochem* 22: 401–413 (1974).
Fiers et al., *Nature* 273: 113–120 (1978).
Frohman et al., *Proc Natl Acad Sci USA* 85: 8998–9002 (1988).
Fujiwara et al., *J Biol Chem* 265: 11333–11337 (1990).
Gabay et al., *J Immunol* 143: 1358–1365 (1989)*.
Ganz et al., *Eur J Haematol* 44: 1–8 (1990).
Ganz et al., *J Clin Invest* 76: 1427–1435 (1985).
Ganz et al., *J Immunol* 143: 1358–1365 (1989).
Geller and Thung, *Arch Pathol Lab Med* 107: 476–479 (1983).
Goeddel et al., *Nucleic Acids Res* 8: 4057–4074 (1980).
Graham and van der Eb, *Virology* 52: 456–467 (1973).
Gyllensten and Erlich, *Proc. Natl. Acad. Science USA* 85: 7652–7656 (1988).
Hertzog, *Am J Pathol* 13: 351–360 (1937).
Hill et al., *Science* 251: 1481–1485 (1991).
Hitzeman et al., *J Biol Chem* 255: 12073–12080 (1980).
Holland, M.J. et al., *J Biol Chem* 256: 1385–1395 (1981).
Holland et al., *Biochemistry* 17: 4900–4907 (1978).
Hsiao, C.L., et al., *Proc Natl Acad Sci USA* 76: 3829–3833 (1979).
Innis et al., *Proc Natl Acad Sci USA* 85: 9436–9440 (1988).
Joiner et al., *J Cell Biol* 109: 2771–2782 (1989).
Kagan et al., *Proc Natl Acad Sci USA* 87: 210–214 (1990).
Keshav et al., *J Exp Med* 171: 327–332 (1990).
Klockars and Reitamo, *J Histochem Cytochem* 23: 932–940 (1975).
Kozak, *J Cell Biol* 115: 887–903 (1991)*.
Lehrer, *Hematol Oncol Clin North Am* 2: 159–169 (1988).
Lehrer et al., *J Virol* 54: 467–472 (1985).
Lehrer et al., *Cell* 64: 229–230 (1991).
Lehrer et al., *J Clin Invest* 84: 553–561 (1989).
Lendrum, *J Pathol Bacteriol* 59: 399–404 (1947).
Lichtenstein, *J Clin Invest* 88: 93–100 (1991).
MacLeod et al., *Proc Natl Acad Sci* 88: 552–556 (1991).
Mars et al., *Blood* 71: 1713–1719 (1988).
Mars et al., *Leukemia* 1: 167–172 (1987)*.
Maxam et al., *Methods in Enzymology* 65: 499–560 (1980).
McBride et al., *Clinical Chem* 35: 2196–2201 (1989).
McDermid et al., *Genomics* 5: 1–8 (1989).
Messing et al., *F. Supp. Nucleic Acids Res.* 9: 309–321 (1981).
Matteucci et al., *J Am Chem Soc* 103: 3185–3191 (1981).
Myers et al., *Nature* 313: 495–498 (1985).
Myers et al., *Science* 230: 1242–1246 (1985).
Nakamura et al., *J Biol Chem* 263: 16709–16713 (1988).
Ohara et al., *Proc Natl Acad Sci USA* 86: 5673–5677 (1989).
Okrent et al., *Am Rev Respir Dis* 141: 179–185 (1990).
Olson and Samuelsson, *Acta Chem Scand* 26: 585–595 (1972).
Ouellette and Cordell, *Gastroenterol* 94: 114–121 (1988)*.
Ouellette and Lualdi, *J Biol Chem* 265: 9831–9837 (1990).
Ozaki et al., *J Biochem* 87: 549–555 (1980).
Paterson and Watson, *Am J Pathol* 38: 243–249 (1961).
Peeters and Vantrappen, *Gut* 16: 553–558 (1975).
Proudfoot and Brownlee, *Nature* 263; 211–214 (1976).
Reed and Mann, *Nucl Acids Res* 13: 7207–7221 (1985).
Rice, *Blood* 70: 757–765 (1987).
Riesner et al., *Electrophoresis* 10: 377–389.
Romeo et al., *J Biol Chem* 263: 9573–9575 (1988).
Rosenbaum and Riesner, *Biophys Chem* 26: 235–246 (1987).
Rossiter and Caskey, *J Biol Chem* 265 (22): 12753–12756 (1990).
Saiki et al., *Science* 239: 487–491 (1988).
Sambrook et al., *Molecular Cloning: A Laboratory Manual* Cold Spring Harbor, Cold Spring Harbor Laboratory Press (1989)*.
Sandow and Whitehead, *Gut* 20: 420–431 (1979).
Sanger, F. et al., *Proc Natl Acad Sci USA* 74: 5463–5467 (1977).
Satoh et al., *Anatom Rec* 225: 124–132 (1989).
Satoh and Vollrath, *Anat Embryol* 173: 317–322 (1986).
Satoh et al., *Digestion* 34: 115–121 (1986).
Schowalter et al., *Genomics* 6: 23–32 (1990).
Selsted et al., *Infect Immun* 45: 150–154 (1984).
Selsted and Harwig, *Infect Immun* 55: 2281–2286 (1987).
Selsted et al., *J Biol Chem* 260: 4579–4584 (1985).
Selsted et al., *J Clin Invest* 76: 1436–1439 (1985).
Selsted et al., *J Biol Chem* 258: 14485–14489 (1983).
Selsted and Harwig, *J Biol Chem* 264: 4003–4007 (1989).
Shaw, CH., et al., *Gene* 23: 315–330 (1983).
Shigenaga et al., *J Biol Chem* 265: 21350–21354 (1990).
Shimatake et al., *Nature* 292: 128–132 (1981).
Singh et al., *Bioch Biophys Res Commun* 155: 524–529 (1988).
Spitznagel, *J. Clin Invest* 86: 1381–1386 (1990).
Stinchchomb et al., *Nature* 282: 39–43 (1979).
Steiner et al., *Nature* 292: 246–248 (1981).
Stoflet et al., *Science* 239: 491–494 (1988).
Territo et al., *J Clin Invest* 84: 2017–2020 (1989).
*Tissue Cultures,* Academic Press, Cruz and Patterson, editors (1978)*.
Trier, *J Cell Biol* 18: 599–620 (1963).
Van Solingen, P., et al., *J Bact* 130: 946–947 (1977).
Wiedemann et al., *Leukemia* 3: 227–234 (1989).
Wilde et al., *J Biol Chem* 264: 11200–11203 (1989).
Zasloff, *Proc. Natl Acad Sci USA* 84: 5449–5453 (1987).

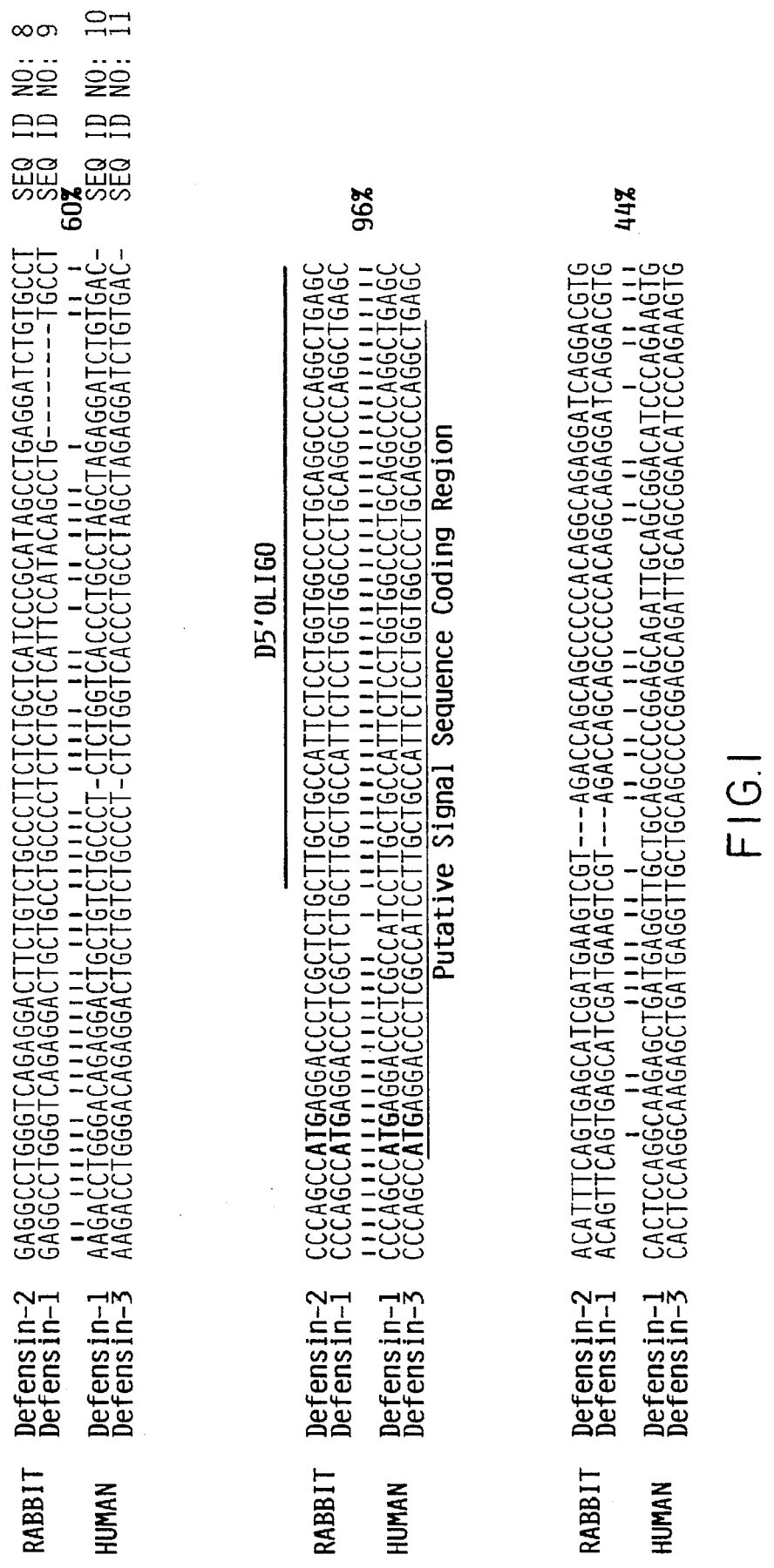

```
RABBIT  Defensin-2  GAGGCCTGGGTCAGAGGACTTCTGTCTGCCCTTCTCTGCTCATCCCGCATAGCCTGAGGATCTGTGCCT   SEQ ID NO: 8
        Defensin-1  GAGGCCTGGGTCAGAGGACTGCTGCCTGCCCCTCTCTGCTCATTCCATACAGCCTG--------TGCCT   SEQ ID NO: 9
                                                                                         60%
HUMAN   Defensin-1  AAGACCTGGGACAGAGGACTGCTGTCTGCCCT-CTCTGGTCACCCTGCCTAGCTAGAGGATCTGTGAC-   SEQ ID NO: 10
        Defensin-3  AAGACCTGGGACAGAGGACTGCTGTCTGCCCT-CTCTGGTCACCCTGCCTAGCTAGAGGATCTGTGAC-   SEQ ID NO: 11

                                                           D5'OLIGO
RABBIT  Defensin-2  CCCAGCCATGAGGACCCTCGCTCTGCTTGCTGCCATTCTCCTGGTGGCCCTGCAGGCCCAGGCTGAGC
        Defensin-1  CCCAGCCATGAGGACCCTCGCTCTGCTTGCTGCCATTCTCCTGGTGGCCCTGCAGGCCCAGGCTGAGC
                                                                                        96%
HUMAN   Defensin-1  CCCAGCCATGAGGACCCTCGCCATCCTTGCTGCCATTCTCCTGGTGGCCCTGCAGGCCCAGGCTGAGC
        Defensin-3  CCCAGCCATGAGGACCCTCGCCATCCTTGCTGCCATTCTCCTGGTGGCCCTGCAGGCCCAGGCTGAGC
                                   Putative Signal Sequence Coding Region

RABBIT  Defensin-2  ACATTTCAGTGAGCATCGATGAAGTCGT---AGACCAGCAGCCCCCACAGGCAGAGGATCAGGACGTG
        Defensin-1  ACAGTTCAGTGAGCATCGATGAAGTCGT---AGACCAGCAGCCCCCACAGGCAGAGGATCAGGACGTG
                                                                                        44%
HUMAN   Defensin-1  CACTCCAGGCAAGAGCTGATGAGGTTGCTGCAGCCCCGGAGCAGATTGCAGCGGACATCCCAGAAGTG
        Defensin-3  CACTCCAGGCAAGAGCTGATGAGGTTGCTGCAGCCCCGGAGCAGATTGCAGCGGACATCCCAGAAGTG
```

FIG. 1

SEQ ID NO: 1

```
caaatatagagactctccaagggcccactgagccccaaaggatttggatcaaatatggtg  60
atattatggaaatatgtagtaatatcttaaaaatgtgtaagatatagtctcttttttttt  120
ttttttaagagaaggggtctcactatgtttttaggctggtatcgaactcctggtctccag  180
tgatcctcccacctcagcctgtcaaatagctagaaatataggcatgtaccaccatgctgg  240
cttaagatgcattctttgacacagcaattctatttctataagtttatccatataggtaag  300
agaacatatatacaagataatcactgtaactttacttattactgcaaaagtttaaaaata  360
accaaattgtaataattttataatattttatcagtacaaaaaataagtgatggcatatac  420
aaaccctgggatagtataaggctattaaaattataatagcattccatgtattttgatata  480
caaagtgccaatgttacaggtgaaaaaagcgaagtgcagaatactatgtgtaactgttaa  540
tagtgatggtttgctgggtcagaactgaaggcctgggggtagaaatgagagctcatgact  600
tctaccttttgaatgttgttccttgtgcatgatttacaattttctaaaactaaaaaaaaa  660
atctcagaaaggggctgtacgcacctaaattactttgatattccccaaagtggagagaag  720
tacccgctacacattttatgtgatgcattcagatcacaccaactccttgaactaaatccg  780
aatttttattttaatctgataaacttggcctactattttactgaactcatttcccctata  840
gcctgataaggtcattgacctctccatactggcaccagcgggagactactcacctcgaga  900
tctcaaaagcctcctacatgaggttagtaatatccctgaatcctgcaatgaattaactct  960
ctactccactgggtcccaggtctgcccccagagagtcatccagagagtaccagggaccat  1020
cttcagaaaacaagaggcatttgatccccaaacttcttgaatgaaagcgctgttgttttt  1080
ctttttgaatatataaaagtaaatactcaagcagatgggaaacagaacaggatagtaat  1140
acccttatcatcattaacaccttggatcaagaagaggcattaagcatacagactcacgct  1200
ttgatgaaagctgggagaaagaggagcatcaaagggatcttgagaacaaaggcagtcctt  1260
cccctcccaatcacatgcccacctcctctcactgcagcttctgtctcaggtcttctccca  1320
gcagagctataaatccaggctgactcctcactccccacATATCCACTCCTGCTCTCCCTC  1380
CTGCAGGTGACCCCAGCCATGAGGACCATCGCCATCCTTGCTGCCATTCTCCTGGTGGCC  1440
                        MetArgThrIleAlaIleLeuAlaAlaIleLeuLeuValAla

CTGCAGGCCCAGGCTGAGTCACTCCAGGAAAGAGCTGATGAGGCTACAACCCAGAAGCAG  1500
LeuGlnAlaGlnAlaGluSerLeuGlnGluArgAlaAspGluAlaThrThrGlnLysGln
```

FIG. 2B-1

```
TCTGGGGAAGACAACCAGGACCTTGCTATCTCCTTTGCAGGAAATGGACTCTCTGCTCTT  1560
SerGlyGluAspAsnGlnAspLeuAlaIleSerPheAlaGlyAsnGlyLeuSerAlaLeu

AGAACCTCAGgtaggagacatcaatcttgcacatctgcaaaatctagaaaaaaaggattg  1620
ArgThrSerG(ly)

gagaaaggatctggagtcaagtgtggaaaggtctacctcacttgagtgactttacttaat  1680

cttcctggaccttgattttctcatctataaattaatcagtgagaaccaaataaatctaaa  1740

agatttttctttttttctaagactttcagctccaagatatttctgtgaaatttgctactttt  1800

aagatagaaagagctacactgactagttctttgtagatctaaatgggcagacttagttat  1860

atagagagtgttttactttgtccattggaaaagcttttagaacctagagaggaacctata  1940

ggtgtgttttgatgtaggctaataggcttgattaaatctttctacaatacatccttagat  2000

caaaacatcatattgtgtctcatacatatacacaattattgtttgtcaattaaaacaagt  2060

aaatatgtaaaatgttaaaaaaaaaaaaaaaaaaaaaggagagacagagaatgaagaat  2120

ttgaatttggaaagtcttcaaagactccttgagcaccaaagtatttggtccatgacatta  2180

gcatgcacaatgcggcatttcagaaactgattcaggtgctttagggagccttgttaggac  2240

ctggaaatcacacatggaggtcaagattaggcgtgtggatgaagcagaatgaagagtagg  2300

taaccctgaggttgagaggtatattgttggaccagggagcaggtaataaatacatcctgg  2360

atagactcacatggggaaaaaaactatgatcttgcatgactaacacatagctagtaagat  2420

ttcttgtcacttacgacaaagacatgaattttctccatcctaacatgactgatacagtgt  2480

ctcttatttagactatctcagttagtctggctgtgcttgtcctttttcccacctccctcg  2540

ctgtgcctgaccctctcttctttccacagGTTCTCAGGCAAGAGCCACCTGCTATTGCCG  2600
                             (g)lySerGlnAlaArgAlaThrCysTyrCysAr

AACCGGCCGTTGTGCTACCCGTGAGTCCCTCTCCGGGGTGTGTGAAATCAGTGGCCGCCT  2660
gThrGlyArgCysAlaThrArgGluSerLeuSerGlyValCysGluIleSerGlyArgLe

CTACAGACTCTGCTGTCGCTGAGCTTCCTAGATAGAAACCAAAGCAGTGCAAGATTCAGT  2720
uTyrArgLeuCysCysArgOpal

TCAAGGTCCTGAAAAAAGAAAAACATTTTACTCTGTGTACCTTGTGTCTTTCTAAATTTC  2780

TCTCTCCAAAATAAAGTTCAAGCATTaaacttagtgtgtttgacctttttaattttcttt  2840

tctttttcctttttttttcttttgctttgttatatggtggtttgtatggttcctttgtatt  2900
```

FIG. 2B-2

| | | SEQ ID NO: |
|---|---|---|
| CTTGCTGCCATTCTCCTGGTGGCCCTGCAGGCCCAGGCTGAGC | - **PROBE** | 35 |
| ::::::::::::::::::::::::::::::::::::::::::: | clones 1 & 2 | 35 |
| ::CA::::TG::::::C::::::::C::::::A:::::::::: | clones 3 & 4 | 50 |

FIG.4B

SEQ ID NO: 4

ATATCCACTCCTGCTCTCCCTCCTGCAGGTGACCCCAGCCATGAGGACC 49
M R T

ATCGCCATCCTTGCTGCCATTCTCCTGGTGGCCCTGCAGGCCCAGGCTGAG 100
I A I L A A I L L V A L Q A Q A E

TCACTCCAGGAAAGAGCTGATGAGGCTACAACCCAGAAGCAGTCTGGGGAA 151
S L Q E R A D E A T T Q K Q S G E

GACAACCAGGACCTTGCTATCTCCTTTGCAGGAAATGGACTCTCTGCTCTT 202
D N Q D L A I S F A G N G L S A L

AGAACCTCAGGTTCTCAGGCAAGAGCCACCTGCTATTGCCGAACCGGCCGT 253
R T S G S Q A R A T C Y C R T G R

TGTGCTACCCGTGAGTCCCTCTCCGGGGTGTGTGAAATCAGTGGCCGCCTC 304
C A T R E S L S G V C E I S G R L

TACAGACTCTGCTGTCGCTGAGCTTCCTAGATAGAAACCAAAGCAGTGCAA 355
Y R L C C R End

GATTCAGTTCAAGGTCCTGAAAAAAGAAAAACATTTTACTCTGTGTACCTT 406

GTGTCTTTCTAAATTTCTCTCTCCAAAATAAAGTTCAAGCATTAAAAAA 455

FIG.4C

FIG. 5B
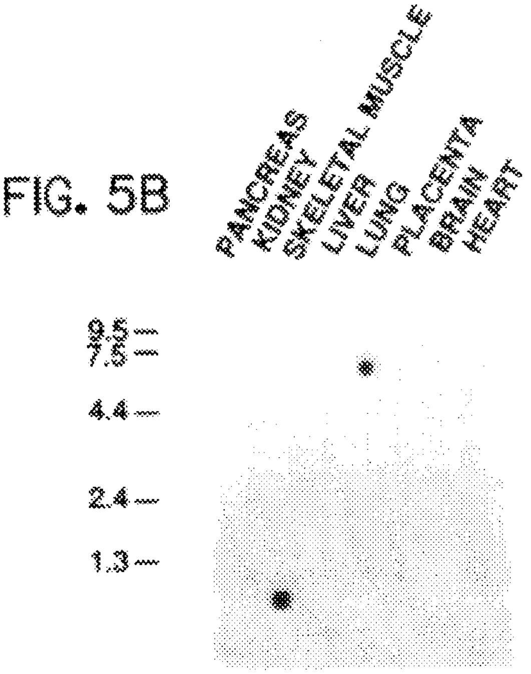
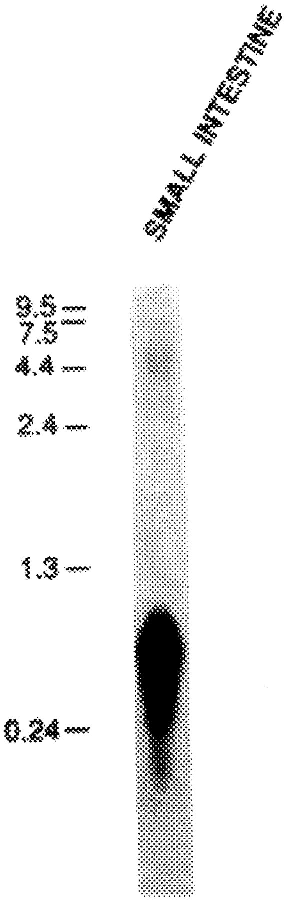
FIG. 5A
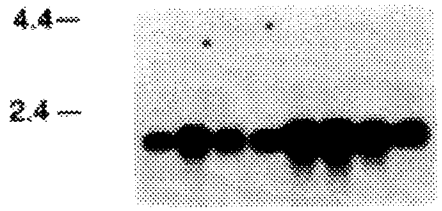
FIG. 5C
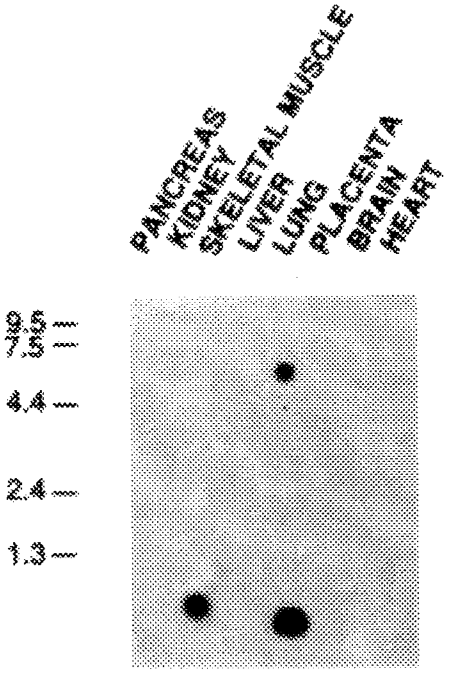
FIG. 5D

SIGNAL SEQUENCE                             PROPEPTIDE

```
       +         -   -+ -             -      +     -- -
MRTIAILAAILLVALQAQAESLQERAD-------E-ATTQKQSGEDNQDLAISFAGNGL--
    ::  :: :  :::::::: :: ::        :        ::  ::   :  ::
MRTLTILTAVLLVALQAKAEPLQAEDDPLQAKAYE-ADAQEQRGANDQDFAVSFAEDAS--

 :::   ::::::::::::::::: :::::                    ::  ::
MRTLAILAAILLVALQAQAEPLQARAD-------EVAAAPEQIAADIPEVVVSLAWDE---

 :::  ::::::::::::::::::                          :  ::
MRTLALLAAILLVALQAQAEHVSVSID-------EVVDQQPPQAED-QDVAIYV-KEHES-
               I

 :  ::::  ::  ::   ::   :                          :::
MKKLVLLFALVLLGFQVQADSIQNT-D-------EETKTEEQPGEEDQAVSVSF-GDPEGT

MrtLa LaAilLvalQaQAe   q     D         E      q e q v  s
```

FIG.6A

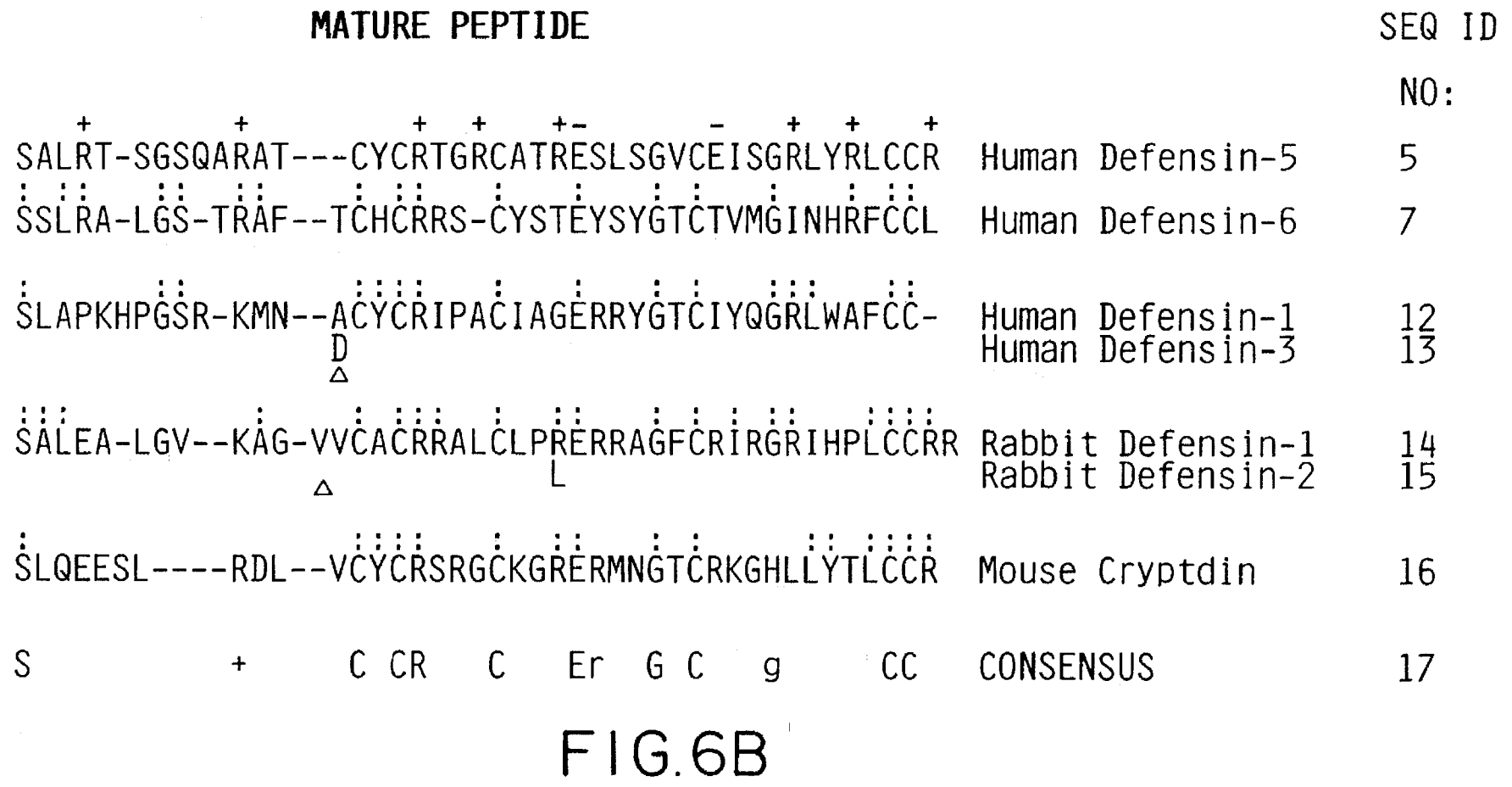

| MATURE PEPTIDE | | SEQ ID NO: |
|---|---|---|
| SALRT-SGSQARAT---CYCRTGRCATRESLSGVCEISGRLYRLCCR | Human Defensin-5 | 5 |
| SSLRA-LGS-TRAF--TCHCRRS-CYSTEYSYGTCTVMGINHRFCCL | Human Defensin-6 | 7 |
| SLAPKHPGSR-KMN--ACYCRIPACIAGERRYGTCIYQGRLWAFCC- | Human Defensin-1 | 12 |
| D | Human Defensin-3 | 13 |
| SALEA-LGV--KAG-VVCACRRALCLPRERRAGFCRIRGRIHPLCCRR | Rabbit Defensin-1 | 14 |
| L | Rabbit Defensin-2 | 15 |
| SLQEESL----RDL--VCYCRSRGCKGRERMNGTCRKGHLLYTLCCR | Mouse Cryptdin | 16 |
| S + C CR C Er G C g CC | CONSENSUS | 17 |

FIG.6B

GASTROINTESTINAL DEFENSINS, CDNA SEQUENCES AND METHOD FOR THE PRODUCTION AND USE THEREOF

This is a continuation of application Ser. No. 07/888,232, filed May 22, 1992.

REFERENCE TO GOVERNMENT GRANTS

Research for this invention was supported in part by National Institutes of Health Grant 5T32GM07170. The United States government may have certain rights in the invention.

FIELD OF THE INVENTION

The present invention relates generally to defensin peptides referred to herein as gastrointestinal defensin peptides. More particularly, the present invention is related to new members of a class of polypeptide with antimicrobial and anti-inflammatory activity, cDNA and genomic sequences encoding for the peptides, methods for the production and use thereof.

BACKGROUND OF THE INVENTION

Multicellular organisms utilize a variety of mechanisms to defend against microbial invasion. These include anatomical and chemical barriers, as well as numerous cell-mediated and humoral responses. Collectively these defenses aim to eliminate offending microorganisms. Epithelial surfaces of many tissues are continually exposed to potential pathogenic organisms, yet the incidence of infectious disease following these encounters is relatively small, highlighting the effectiveness of defense mechanisms at these sights. Manifestations of abnormality of these defenses in the intestinal tract may include various forms of diarrhea associated with pathogenic bacteria and ulcerative diseases including inflammatory bowel disease, necrotizing enterocolitis and gastric ulcer disease.

Peptide based antimicrobial defense is a conserved component of host defense, and is found in both the animal and plant kingdoms (for reviews see Boman and Hultmark, *Ann Rev. Microbiol.*, 41: 103–126 (1987); Bevins and Zasloff, *Ann Rev. Biochem*, 59:395–414 (1990); Spitznagel, *J Clin. Invest.* 86: 1381–86 (1990); Boman, Cell 65: 205–207 (1991); Lehrer et al., *Cell* 64: 229–230 (1991)). The size and structure of the antimicrobial peptides shows significant diversity, but in general, they are membrane-active amphipathic molecules with a net positive charge at neutral pH. There are two broadly defined families of these cationic peptides: linear peptides (for example cecropins; Steiner, et al., *Nature* 292: 246–248 (1981); and magainins; (Zasloff, *Proc. Natl. Acad. Sci.* USA 84: 5449–5453 (1987)) and cystsine-rich peptides. The latter include mammalian defensins (Ganz et al., *Eur J Haematol* 44: 1–8 (1990)), tracheal antimicrobial peptide (Diamond, et al., *Proc Natl Acad Sci* (USA) 88:3952–3956 (1991), bovine bactenecins, (Romeo et al. *J Biol Chem* 263: 9573–9575 (1988)), insect royalisin, (Fujiwara et al., *J Biol Chem* 265:11333–11337 (1990)), tachyplesins (Nakamura, et al., *J Biol Chem* 263:16709–16713 (1988); Shigenaga, et al., *J. Biol Chem* 265: 21350–21354 (1990), and plant thionins (Olson and Samuelsson, *Acta Chem Scand* 26: 585–595 (1972); Ozaki, et al., *J. Biochem* 87:549–555 (1980); Bohlmann and Apel, *Mol Gen Genetics* 207: 446–454 (1987); Bohlmann, et al., *EMBO J* 7: 1559–1565 (1988).

Defensins are cysteine-rich basic peptides which have been isolated from myeloid-derived cells of several mammalian species (For recent reviews see Ganz, et al., *Eur J Haematol* 44:1–8 (1990); Lehrer, et al., *Cell* 64: 229–230 (1991). Defensins have in vitro antimicrobial activity against bacteria; Selsted, et al., *Infect Immun* 45: 150 (1984); Ganz, et al., *J Clin Invest* 76: 1427–1435 (1985); fungi; Ganz, et al., *J Clin Invest* 76: 1427–1435 (1985); Borenstein, et al., *Infect Immun* 59: 1359–67 (1991); and enveloped viruses (Lehrer et al., *J Virol* 54: 467 (1985); Daher, et al., *J Virol* 60: 1068–1074 (1986). Defensins are characterized by eleven conserved residues within the sequence, including six cysteines which participate in intramolecular disulfide bonds (Selsted and Harwig, *J Biol Chem* 264:4003–4007 (1989). This disulfide array is important for structure and activity of defensins. Evidence suggests that their antimicrobial activity is a direct result of their ability to selectively disrupt membranes (Lehrer, et al., *J Clin Invest* 84:553–561 (1989)); Lichtenstein, *J Clin Invest* 88: 93–100 (1991), possibly by channel formation (Kagan, et al, *Proc Natl Acad Sci* (USA) 87: 210–214 (1990)). The high-resolution crystal structure of human defensin-3 has recently been determined (Hill, et al. *Science* 251: 1481–1485 (1991), and suggests several specific models for the interaction of defensins with lipid membranes, the site of defensin antimicrobial activity. In addition to antimicrobial activity, certain defensins have other biological activities including, monocyte chemotaxis (Territo, et al., *J Clin Invest* 84: 2017–2020 (1989), adrenocortical suppression (Singh et al., *Bioch Biophys Res Commun* 155: 524–529 (1988), nifedipine-sensitive calcium channel activation (MacLeod et al., *Proc Natl Acad Sci* 88: 552–556 (1991) and eucaryotic cell cytotoxicity (Okrent et al., *Am Rev Respir Dis* 141: 179–185 (1990). In addition to myeloid expression, recent investigations in the mouse (Ouellette and Cordell, *Gastroenterol* 94: 114–121 (1988), Ouellette et al., *J Cell Biol* 108: 1687–1695 (1989), Ouellette and Lualdi, *J Biol Chem* 265: 9831–9837 (1990) and in the cow (Diamond and Bevins, (*In preparation*) (1991)), Diamond et al., *Proc Natl Acad Sci* (USA) 88:3952–3956 (1991) show that the defensin-related peptides, cryptdin and tracheal antimicrobial peptide, are also expressed in epithelial tissues.

In humans, defensins are major constituents of the azurophilic granules of neutrophils (Ganz, et al., *J Clin Invest* 76: 1427–1435 (1985), Selsted, *J Clin Invest* 76: 1436–1439 (1985); Rice, *Blood* 70: 757–765 (1987), Lehrer, *Hematol Oncol Clin North Am* 2: 159–169 (1988) and are though to contribute to the non-oxidative killing of microorganisms by these circulating leukocytes. (Lehrer et al., *Hematol Oncol Clin North Am* 2: 159–169 (1988). Defensins and other proteins of the azurophilic granules have been shown to enter the phagolysosome vesicles of neutrophils during phagocytosis of bacteria (Joiner et al., *J Cell Biol* 109: 2771–2782 (1989). Four myeloid-derived human defensins have been isolated and characterized (Ganz et al., *J Clin Invest* 76: 1427–1435 (1985); Selsted, et al., *J Clin Invest* 76:1436–1439 (1985); Singh et al, *Bioch Biophys Res Commun* 155: 524–529 (1988), Gabay et al., *J Immunol* 143:1358–1365 (1989), Wilde, *J Biol Chem* 264:11200–11203 (1989). Human defensins 1 and 3 are 30 amino acid peptides, differing in sequence by only a single residue at their amino terminus. (Selsted, et al., *J Clin Invest* 76:1436–1439 (1985). The cloned cDNAs for these two defensins (Daher, et al., *Proc Natl Acad Sci* USA 85:7327–7331 (1988); Mars et al., *Blood* 71: 1713–1719 (1988); Wiedemann et al., *Leukemia* 3: 227–234 (1989) are greater than 98% identical in nucleotide sequence, with a single nucleotide difference in codon 65 of the putative prepropeptides accounting for the alanine or aspartic acid residues in the mature defensins 1 and 3 respectively. Defensin 2, a 29 amino acid peptide, is identical to defensins 1 and 3 except that it lacks either of these amino acids at its amino-terminus (Selsted, et al., *J Clin Invest* 76: 1436–1439 (1985). The cDNA for this defensin has not yet been cloned, and it is not clear if it is a product of a distinct gene, or a post-translational proteolytic modification of defensins 1 or 3. Defensin 4 is quite different from other human defensins in primary structure. This 33 residue peptide essentially shares only the consensus residues that characterize defensins (Singh et al., *Bioch Biophys Res Commun* 155: 524–529 (1988); Wilde, et al., *J Biol Chem* 264; 11200–11203 (1989), and neither its cDNA or gene have been described. By in situ hybridization histochemistry, defensin cDNA probes detect a message expressed in a relatively narrow window of granulocyte development. The mRNA is abundant in late promyelocytes and early myelocytes, precursors of the mature circulating neutrophils (Mars et al., *Leukemia* 1: 167–172 (1987), Wiedemann, et al., *Leukemia* 3: 227–234 (1989), as well as other granular leukocytes (Mars, et al. *Leukemia* 1: 167–172 (1987) of human bone marrow, but is undetectable by northern blot analysis in circulating neutrophils (Daher, et al., *Proc Natl Acad Sci* USA 85:7327–7331 (1988).

Novel defensin peptides having antimicrobial and anti-inflammatory activity are greatly desired. Defensin peptides particularly suitable for use in the gastrointestinal tract of humans are particularly desireable since they may be effective for treatment of gastrointestinal conditions such as various forms of diarrhea associated with pathogenic bacteria and ulcerative diseases including inflammatory bowel syndrome, necrotizing enterocolitis and gastric ulcer disease.

SUMMARY OF THE INVENTION

The primary sequence of endogenous host defense peptides reflects evolutionary selection for chemical properties necessary for high activity of peptides in a specific local environment. Defensin peptides endogenous to the human gastrointestinal tract are believed to be suitable for pharmacological use in this organ system and are particularly desirable since they may be effective for treatment of gastrointestinal conditions such as bacterial diarrhea, gastric ulcer disease related to Helicobacter pylori, inflammatory bowel disease, and necrotizing enterocolitis. Furthermore the nucleotide sequence of cDNAs and genes encoding endogenous defensin peptides contain important information for regulated expression. This information can be exploited pharmacologically to alter endogenous expression. These nucleotide sequences can be used diagnostically to detect mutations in these genes and to assess biopsy materials.

Thus, the present invention provides novel defensin peptides endogenously localized in the gastrointestinal tract which may be useful for treatment of microbial infection and gastrointestinal inflammation.

In accordance with some embodiments of the present invention, substantially pure gastrointestinal defensin peptides are provided comprising at least a portion of an amino acid sequence as defined in SEQ ID NO:5 or SEQ ID NO:7. In other embodiments of the present invention gastrointestinal defensin peptides which are produced from cDNA sequences comprising at least a portion of the sequence defined in SEQ ID NO:4 or SEQ ID NO:6 are provided. Recombinant expression vectors are provided which are capable of expression in a suitable expression system comprising a DNA sequence encoding a gastrointestinal defensin peptide linked to control sequences compatible with the selected expression system. Gastrointestinal defensin peptides produced from such vectors are also provided by the present invention. Contact disinfectants are provided in some embodiments of the present invention comprising an effective amount of a gastrointestinal defensin peptide. In still other embodiments of the present invention pharmaceutical compositions are provided comprising gastrointestinal defensin peptides in a pharmaceutically acceptable carrier. Methods of treating microbial infection and gastrointestinal inflammation are provided in other embodiments of the present invention whereby an antimicrobially effective amount of a gastrointestinal defensin peptide is administered to mammals suffering from a microbial infection or gastrointestinal inflammation. Also provided by the present invention are methods of diagnosing microbial infection of the gastrointestinal tract whereby a sample is taken from a patient and the amount of defensin peptide or mRNA coding for the defensin peptide present in the sample is detected. The amount of gastrointestinal defensin peptide or mRNA in the sample is compared to the amount peptide or mRNA present in a normal mammalian gastrointestinal tract whereby greater or lesser quantities of gastrointestinal defensin peptide or mRNA is indicative of the likelihood of infection. Similarly methods of diagnosing gastrointestinal inflammation are provided whereby a sample is taken from a patient and the amount of defensin peptide or mRNA coding for the defensin peptide present in the sample is detected. The amount of gastrointestinal defensin peptide or mRNA in the sample is compared to the amount peptide or mRNA present in a normal mammalian gastrointestinal tract whereby greater or lesser quantities of gastrointestinal defensin peptide or mRNA is indicative of the likelihood of inflammation. In accordance with other methods of the present invention, the susceptibility of a patient to gastrointestinal disorders may be diagnosed by providing a DNA containing test sample from a human patient and amplifying the DNA from the DNA-containing test sample using an upstream probe having a sequence complementary to an upstream portion of a defensin sequence selected from the group consisting of SEQ ID NO: 1, SEQ ID NO: 4 and SEQ ID NO: 5 and a downstream probe having a sequence complementary to a downstream portion of the selected defensin sequence. The amplified DNA and DNA from a normal sample may be compared to identify mutation of the amplified DNA as compared to normal DNA whereby mutation is indicative of the likelihood that the patient has increased susceptibility to gastrointestinal disorders. A method of identifying a defensin is also provided whereby a library of genomic clones is screened using an oligonucleotide probe derived from evolutionarily conserved defensin sequences. Hybridization of the probe to a clone indicates the likelihood that the clone contains a DNA sequence coding for a defensin peptide. The clone is characterized in some embodiments of the present invention to determine the DNA sequence of the defensin peptide.

It is therefore an object of the present invention to provide substantially pure gastrointestinal defensin peptides. It is another object of the invention to provide pharmaceutical compositions useful for the treatment of gastrointestinal microbial infection and inflammation. It is still a further object of the present invention to provide methods of treating and preventing gastrointestinal microbial infections. It is yet a further object of the present invention to provide methods of treating and preventing gastrointestinal inflammation. Methods of diagnosing gastrointestinal microbial infections and gastrointestinal inflammation are also objects of the present invention. Methods of diagnosing a patients susceptibility to gastrointestinal disorders are also an object of the invention. It is yet another object of the present invention to provide methods of identifying defensin peptides. These and other objects will become apparent through a reading the detailed description and attached claims.

BRIEF DESCRIPTION OF THE DRAWINGS

FIG. 1 is a nucleotide sequence comparison of the 5' portion of cDNAs encoding rabbit defensin-1, rabbit defensin-2, human defensin-1 and human defensin 3. Short gaps were included to aid sequence comparison and were considered as mismatches when calculating percentage identity. The sequences for human defensin-1 (Daher, et al., *Proc Natl Acad Sci* USA 85:7327–7331 (1988); Mars et al., *Blood* 71:1713–1719 (1988) and human defensin-3 (Daher, et al., *Proc Natl Acad Sci* USA 85:7327–7331 (1988); Wiedemann, et al., *Leukemia* 3: 227–234 (1989) are identical in the region presented. The sequences for rabbit defensins are from Ganz, et al., *J Immunol* 143: 1358–1365 (1989). Vertical lines denote identical sequences in all four cDNAs. The percentages in the right margin indicate nucleotide identity within the corresponding row. The putative initiating methionine codons are shown in bold, and the nucleotides encoding the putative signal sequence are underlined. The nucleotides corresponding to oligonucleotide probe, D5'oligo, are overlined.

FIG. 2 sets forth the nucleotide sequence of HG2-3e, a genomic clone containing the human defensin 5 gene and flanking sequences. FIGS. 2B-1 and FIG. 2B-2 provide the nucleotide sequence of HG2-3e with numbering in reference to the first nucleotide adjacent to the EcoR1 site. Exon sequences are shown in uppercase lettering and deduced amino acid sequence of the coding region is shown in three letter code. The TATA box is underlined and the CAAT box is double underlined. The consensus splice junction residues are shown in bold. The polyadenylation signal is boxed.

FIG. 3 is data resulting from PCR analysis of possible expression of the human defensin 5 gene in 8 human tissues.

FIG. 4 sets forth characterization of the human defensin 5 cDNA. FIG. 4B is a partial sequence of four clones shown in FIG. 4A in the region corresponding to the probe. Nucleotides identical to the probe are represented by ":". FIG. 4C provides the nucleotide sequence of human defensin 5 cDNA. The sequence represents the composite from the sequences of two lambda cDNA clones (S.I. 25: nucleotides −10 to +415; S.I.34: nucleotides −19 to +413) and two clones from primer extension/RACE PCR (pDJ117-4 and pDJ117-5: −19 to −40), and the putative initiating methionine codon is assigned to +1 to +3. The deduced amino acid sequence of the open reading frame is indicated in a single letter code. The polyadenylation addition signal is boxed.

FIG. 5 is a northern blot hybridization of defensin expression in human tissue. In FIG. 5A total RNA (10 μg) from adult human small intestine was size fractionated in a standard formaldehyde/agarose gel, capillary blotted to a nylon membrane, and probed with a defensin 5 oligonucleotide probe. The condition of stringency for hybridization and final wash were identical to those used in the in situ hybridization experiments described in Example 8. The size markers correspond to RNA standards from a parallel lane. The autoradiographic exposure was 2 days. FIG. 5B is a northern blot of polyadenylation enriched RNA from 8 adult human tissues which was hybridized and washed in the same solution as in FIG. 5A. The exposure was 10 days. The blot was subsequently used in the positive control experiments shown in FIGS. 5B and 5D. The exposure was 3 days. FIG. 5D is a hybridization of the same northern blot as in FIG. 5A with the antisense signal sequence oligonucleotide Sig68a. Bands appear in the lung and placenta lanes. The exposure was 10 days.

FIGS. 6A and 6B are a comparison of deduced amino acid sequence of human preprodefensin 5 and 6 and the putative mature defensin 5 and 6 with known defensin family members. The deduced amino acid sequence of six preprodefensins are from published cDNAs. Cationic residues in human preprodefensin 5 are indicated by "+", and anionic residues by "–". Residues identical to those of preprodefensin 5 are indicated by ":" in the human (Daher, et al., *Proc Natl Acad Sci* USA 85:7327–7331 (1988); Mars et al., *Blood* 71:1713–1719 (1988); Wiedemann et al., *Leukemia* 3: 227–234 (1989), rabbit (Ganz et al., *J Immunol* 143: 1358–1365 (1989) and mouse (Ouellette and Lualid, *J Biol Chem* 265: 9831–9837 (1990) sequences. Human preprodefensins 1 and 3 are identical except for the single amino acid indicated, and the two rabbit sequences are identical except at position 2. The amino terminal residues of the human defensin 1 and 3, and rabbit defensin 1 and 2 are indicated with delta, based on available peptide data (Selsted, et al., *J Biol Chem* 258: 14485–14489 (1983); Selsted, et al., *J Biol Chem* 260:4579–4585 (1985); Selsted, et al. *J Clin Invest* 76: 1436–1439 (1985). No peptide data is yet reported for defensin 5, 6 or mouse cryptdin, and the amino terminus indicated is speculation based on cleavage of two residues from the conserved cationic amino acid in the propeptide as in the other defensins. Short gaps (indicated by "–") were included in the sequences to aid in alignment. A consensus sequence for reported preprodefensins is presented, where an upper case letter denotes identity in all 6 sequences and lower case letters are conserved in 4 (or 5) of the 6.

DETAILED DESCRIPTION OF THE INVENTION

The present invention provides substantially pure polypeptides useful as gastrointestinal antimicrobial and anti-inflammatory agents. The term "antimicrobial" as used herein refers to killing microorganisms or suppressing their multiplication and growth. The term "anti-inflammatory" as used herein refers to inhibition of one or more of the indications associated with inflammation including vasodilation of local blood vessels with consequent excess local blood flow, increased permeability of the capillaries with leakage of large quantities of fluid into the interstitial space, clotting of the fluid in the interstitial space, migration of large numbers of granulocytes and monocytes into the tissue and swelling of the tissue cells. By "substantially pure" as used herein is meant greater than 50% of the material in a composition consists of the desired peptide. Sequences encoding this class of defensin polypeptides were identified based on the observation that the sequences of the 5' portion of the mRNA encoding human and rabbit myeloid-derived defensins have significant nucleotide similarity (FIG. 1). Thus in accordance with methods of the present invention a probe may be constructed based upon evolutionarily-conserved sequences. In preferred embodiments of the present invention a probe (D5'oligo) having the sequence CTTGCTGCCATTCTCCTGGTGGCCCTG-CAGGCCCAGGCTGAGC (SEQ ID NO:35) was used to screen a population of clones to identify novel defensin peptides. In preferred embodiments of the present invention human genomic and cDNA libraries were screened using the D5' oligo probe and a number of clones were isolated. Hybridization and partial sequence analysis demonstrated that within these identified clones were previously characterized myeloid derived defensin sequences as well as new defensin related sequences. Two clones expressing such new defensin related sequences were extensively characterized and found to contain genes selectively expressed in Paneth cells of the small intestine. These Paneth cell-derived defensins are designated human defensin 5 and human defensin 6 and are referred to herein as gastrointestinal defensin peptides. Other gastrointestinal defensin peptides may similarly be identified using these methods.

Figure 2A:
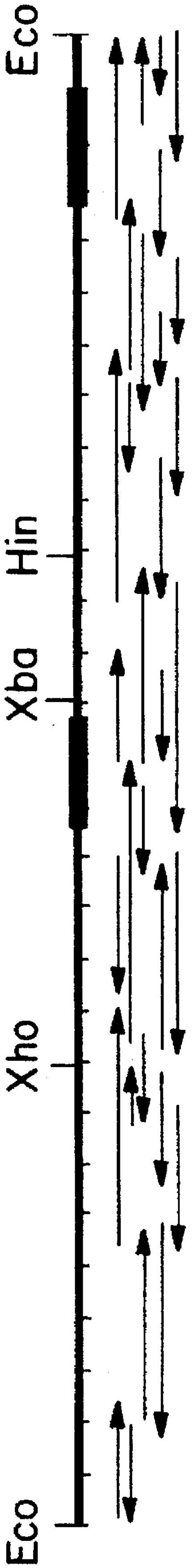
FIG. 2A provides a partial restriction enzyme map of the 2.9 kB EcoR1 fragment, HG2-3e, that encodes human defensin 5 (Eco=EcoR1, Xho=Xho1, Xba=Xba1, Hin=HindIII). Hash marks equal 100 base pairs. The thickened lines shows the position of two exons. The arrows indicate the sequencing strategy used to analyze this clone.

The genomic DNA sequence of Defensin 5 is set forth in FIG. 2. The cDNA sequence and deduced amino acid sequence of Defensin 5 are set forth in FIG. 4. The primary amino acid sequence of mature defensin 5 peptide is set forth in FIG. 7. Comparison of the defensin 5 genomic (FIG. 2) and cDNA (FIG. 4) sequences indicate that the gene as two exons separated by an intron of 994 nucleotides. The nucleotide sequence of the exons in the genomic clone are in complete agreement with those in the cDNA sequence. There are consensus sequences for splice junctions (FIG. 2, bold) and polyadenylation (Proudfoot and Brownlee, *Nature* 263:211–214 (1976) (FIG. 2, boxed). Approximately 1.4 kB of 5' flanking region of this gene was sequenced (FIG. 2). There is a TATA box at nucleotides 1328–1334, 24 nucleotides upstream from the 5' terminus of the two most extended cDNAs identified by RACE-PCR (FIG. 2, underlined). A CAAT box is seen 87 nucleotides upstream from the termini of the extended cDNAs, at position 1267–1271 (FIG. 2, double underlined). The cDNA sequence (FIG. 4) suggests that the mature messenger RNA encoding defensin 5 is 449 nucleotides long, in addition to the polyadenylate tail, which is consistent with the northern blot data (FIG. 5). The cDNA sequence contains an open reading frame of 94 codons in length from the first ATG codon (nucleotides +1 to +3). The context of the methionine codon (CAGCCATGA) is identical to that found in the other two human defensin cDNAs, and is consistent with a favorable translation start sequence (Kozak, *J Cell Biol* 115: 887–903 (1991). The nucleotide sequence encoding the putative signal sequence is 95% identical to the previously cloned human defensin cDNAs, while the nucleotides encoding the remainder of the putative coding region are only 36% identical, consistent with previous observations in the defensin family.

Figure 7:
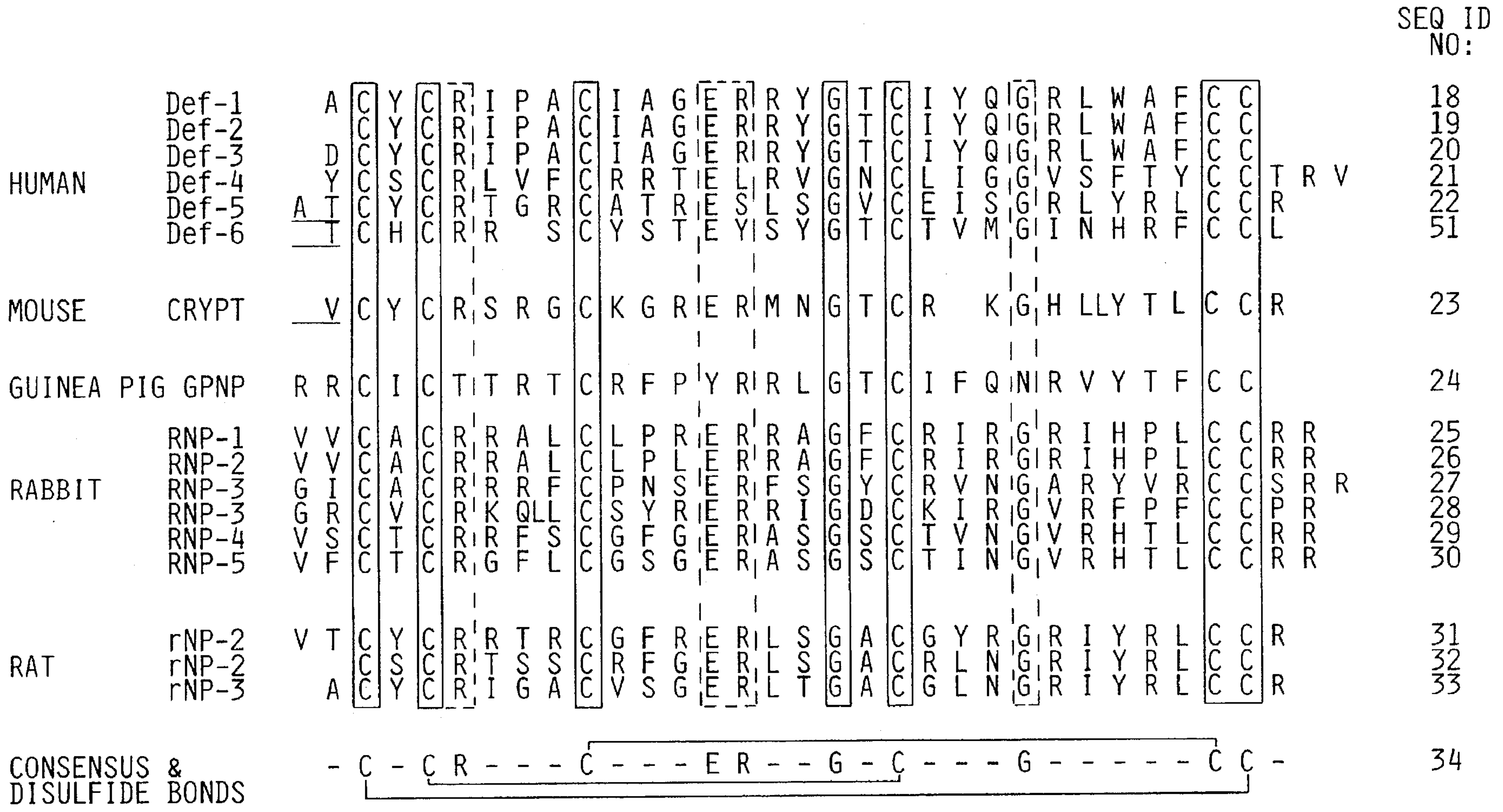
FIG. 7 is the primary sequence of mature defensin peptides from five mammalian species. The format is similar to that presented previously (Hill et al., *Science* 251: 1481–85 (1991); Lehrer et al, *J Virol* 54:467 (1991). Solid boxes indicate sequence identity from published sequence data (Selsted, et al., *J Biol Chem* 258: 14485–14489 (1983); Selsted, et al., *J Biol Chem* 260:4579–4585 (1985); Selsted, et al. *J Clin Invest* 76: 1436–1439 (1985) Selsted and Harwig, *Infect Immun* 55: 2281–2286 (1987); Singh et al., *Bioch Biophys Res Commun* 155:524–529 (1988); Eisenhauer et al., *Immun* 57: 2021–2027 (1989); Ouellette et al., *J Cell Biol* 108:1687–1695 (1989); Wilde et al., *J Biol Chem* 264:11200–11203 (1989), and hashed boxes indicate near perfect consensus. The amino terminal residues of human defensin 5 and mouse cryptdin are underlined to indicate that they are based on cDNA analysis, not peptide data.

Comparison of the deduced amino acid sequences of defensin 5 cDNA with the previously reported preprodefensins shows significant similarity with respect to size and charge distribution (FIG. 6). The carboxyl and amino termini of the putative mature defensin 5 peptide was inferred from patterns emerging from analysis of two rabbit and two human defensins where peptide and cDNA data are available. An in-frame stop codon follows the last residue of all of the peptides. The amino terminal amino acid of the mature peptide is two residues from a conserved cationic amino acid in the putative prepropeptide (FIG. 6). However, sequence comparison to other defensins shows primary structure conservation is not readily predictable by tissue source or species of origin (FIG. 7).

The cDNA and deduced amino acid sequence of Defensin 6 is set forth in SEQ ID NO:6 and 7 respectively. The predicted primary amino acid sequence of mature defensin 6 peptide is set forth in FIG. 7. The deduced amino acid sequence of defensin 6 cDNA has features similar to defensin 5 and the previously reported preprodefensins (FIG. 6). One notable distinction of preprodefensin 6 from the others is the addition of seven amino acid residues at positions 28–33 from the amino terminus. This segment is part of the putative propeptide region, a region that is important in post-translational trafficking and processing in many other peptides systems. Like other defensins, an in-frame stop codon follows the predicted carboxy-terminus, and a cationic propeptide residue is positioned 2 residues from the predicted amino terminus.

The gastrointestinal defensin peptides of the present invention, depending on the pH of the environment, if suspended or in solution, or of its environment when crystallized or precipitates, if in solid form, may be in the form of pharmaceutically acceptable salts or may be in neutral form. The free amino groups of the protein are of course, capable of forming acid addition salts with, for example, organic acids such as hydrochloric, phosphoric, or sulfuric acid or with organic acids such as, for example, acetic, glycolic, succinic, or mandelic acid. The free carboxyl groups are capable of forming salts with bases, including inorganic bases such as sodium, potassium or calcium hydroxides, and such organic bases as piperidine, glucosamine, trimethylamine, choline and caffeine. In addition, the protein may be modified by combination with other biological materials such as lipids and saccharides, or by side chain modification such as acetylation of amino groups, phosphorylation of hydroxyl side chains, or oxidation of sulfhydryl groups.

Modifications of gastrointestinal defensin peptides are included within the scope of the definition, so long as the biological activity is retained. By biological activity is meant among other things, antimicrobial and/or anti-inflammatory activity. Finally it is understood that minor modifications of gastrointestinal defensin peptides may result in proteins which have substantially equivalent or enhanced biological activity as compared to the sequences set forth in SEQ ID NO: 5 and SEQ ID NO:7. These modifications may be deliberate, as through site-directed mutagenesis, or may be accidental such as through mutation in hosts which are gastrointestinal defensin peptide producers. All of these modifications are included as long as the biological activity is retained.

The defensins generally retain certain conserved critical residues of defensin peptides include 6 cysteines which participate in disulfide bonds, arginine -6, glutamic acid-14 and glycine-24. Other residues are believed to be key in dimeric quaternary structure: cystsine-5, glycine-18, cystsine-20, and hydrophobic residues at positions 22 and 28. Defensins 5 and 6 have conservation of all of these critical residues. Based on these sequence similarities, the biological activities, especially antimicrobial activities, of defensin 5 and 6 are believed to echo the biological activities of other defensin peptides. Furthermore, due to the localization of these gastrointestinal defensin peptides and the observed increased concentration of gastrointestinal defensin peptides in the gastrointestinal tract of patients suffering from inflammatory bowel syndrome, these defensins are believed to be related to the modulation of gastrointestinal inflammation.

Experiments using PCR (FIG. 3A) and northern blot analysis (FIG. 5A and 5B) indicate that the defensin 5 gene is limited in its tissue expression. The specific small intestinal cell expressing the defensin 5 gene is the Paneth cell, based on in situ histochemical data. Similarly, defensin 6 is localized in the Paneth cells.

The specific lineage of Paneth cells and their physiological role are not well defined (Sandow and Whitehead, *Gut* 20:420–431 (1979). Paneth cells are found throughout the bowel but are especially abundant in the small intestinal ileum (Hertzog, *Am J Pathol* 13: 351–358 (1937). The cells have abundant rough endoplasmic reticulum, an elaborate golgi apparatus and large secretory vesicles typical of a secretory cell (Trier, *J Cell Biol* 18: 599–620 (1963); Benke and Moe, *J Cell Biol* 22: 633–652 (1964). Metaplasia of these cells has been seen in a variety of pathological conditions in humans (Geller and Thung, *Arch Pathol Lab Med* 107: 476–479 (1983), including inflammatory bowel disease (Paterson and Watson, *Am J Pathol* 38: 243–249 (1961), Several lines of evidence suggest these cells have a role in antimicrobial defense. Paneth cells have been shown to express tumor necrosis factor mRNA (Keshav et al., *J Exp Med* 171: 327–332 (1990) and to contain lysozyme (Paterson and Watson, *Amer J Pathology* 38: 243–249 (1961); Erlandsen et al., *J Histochem Cytochem* 22: 401–413 (1974); Klockars and Reitamo, *J Histochem Cytochem* 23: 932–940 (1975); Peeters and Vantrappen, *Gut* 16: 553–558 (1975). The lysozyme is localized to secretory granules in these cells (Deckx et al., *Biochem Biophys Acta* 139:204–207 (1967); Peeters and Vantrappen, *Gut* 16: 553–558 (1975), and various stimuli have been shown to effect degranulation of these cells (Klockars and Reitamo, *J Histochem Cytochem* 23: 932–40 (1975); Peeters and Vantrappen, *Gut* 16:553–558 (1975); Satoh et al., *Digestion* 34: 115–121 (1986); Satoh and Vollrath, *Anat Embryol* 173: 317–322 (1986); Satoh et al., *Anatom Rec* 222:124–132 (1989). Thus, these finding further substantiate the role of defensin 5 and 6 as antimicrobial and anti-inflammatory peptides. It is believed that other peptides identified using methods of the present invention which are localized to the Paneth cells will also exhibit antimicrobial and anti-inflammatory activity.

Having described the DNA and amino acid sequence of defensin 5 (SEQ ID NO:4 and SEQ ID NO: 5) and defensin 6 (SEQ ID NO:6 and SEQ ID NO:7) it is believed these gastrointestinal defensin peptides or portions thereof may be prepared using modifications of any of numerous well known recombinant techniques such as those described in U.S. Pat. No. 4,677,063 which patent is incorporated by reference as if fully set forth herein. By "portion thereof" as used herein is meant to refer to any portion of a peptide or nucleic acid of sufficient size to retain desired biological activities, and particularly antimicrobial and anti-inflammatory activity. For example, some preferred defensin peptide "portions" are the mature peptides set forth in SEQ ID NO: 22 or SEQ ID NO: 51. Other portions which retain biological activity are also envisioned by the present invention.

Briefly, most of the techniques which are used to transform cells, construct vectors, extract messenger RNA, prepare cDNA libraries, and the like are widely practiced in the art, and most practitioners are familiar with standard resource materials which describe specific conditions and procedures. However, for convenience, the following paragraphs may serve as a guideline.

Procaryotes most frequently are represented by various strains of *E. coli*. However, other microbial strains may also be used, such as Bacilli, for example, *Bacillus subtilis*, various species of Pseudomonas, or other bacterial strains. In such procaryotic systems, plasmid vectors which contain replication sites and control sequences derived from a species compatible with the host are used. In one such "expression system" for example, *E. coli* is transformed using a derivative of pBR322, a plasmid derived from an *E. coli* species by Bolivar, et al., *Gene* 2: 95 (1977). pBR322 contains genes for ampicillin and tetracycline resistance and thus provide additional markers which can be either retained or destroyed in constructing the desired vector. Commonly used procaryotic control sequences include promoters for transcription initiation, optionally with an operator, along with ribosome binding site sequences, include such commonly used promoters as the beta-lactamase (penicillinase) and lactose (lac) promoter systems (Chang, et al., *Nature* 198: 1056 (1977)) and the tryptophan (trp) promoter system (Goeddel, et al., *Nucleic Acids Res* 8: 4057 (1980)) and the lambda derived $P_L$ promoter and N-gene ribosome binding site (Shimatoake, et al., *Nature* 292: 128 (1981)).

In addition to bacteria, eucaryotic microbes, such as yeast may also be used as hosts. Laboratory strains of *Saccharomyces cerevisiae*, Baker's yeast, are most used although a number of other strains are commonly available. While vectors employing the 2 micron origin of replication are illustrated, Broach, J. R., *Meth Enz.* 101: 307 (1983), other plasmid vectors suitable for yeast expression are known (see, for example, Steinchcomb, et al., *Nature* 282: 39 (1979), Tschempe, et al., *Gene* 10: 157 (1980) and Clark, L., et al., *Meth Enz* 101: 300 (1983)). Control sequences for yeast vectors include promoters for the synthesis of glycolytic enzymes (Hess, et al., *J. Adv Enzyme Req* 7: 149 (1968); Holland, et al. *Biochemistry* 17: 4900 (1978)). Additional promoters known in the art include the promoter for 3-phosphoglycerate kinase (Hitzeman, et al., *J. Biol. Chem* 255: 2073 (1980)), and those for other glycolytic enzymes such as glyceraldehyde-3-phosphate dehydrogenase, hexokinase, pyruvate decarboxylase, phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acidphosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al., *J. Biol Chem* 256:1385 (1981)) or the LEU2 gene obtained from YEp13 (Broach, J., et al., *Gene* 8: 121 (1978)), however any vector containing a yeast compatible promoter, origin of replication and other control sequences is suitable.

It is also of course possible to express genes encoding polypeptides in eucaryotic host cell cultures derived from multicellular organisms. See, for example, *Tissue Cultures*, Academic Press, Cruz and Patterson, editors (1973). Useful host cell lines include VERO, HeLa cells, and Chinese hamster ovary (CHO) cells. In vivo expression of genes encoding polypeptides in eucaryotic hosts is also a feasible method of preparation of gastrointestinal defensin peptides.

Expression vectors for such cells ordinarily include promoters and control sequences compatible with mammalian cells such as, for example, the commonly used early and late promoters from Simian Virus 40 (SV 40) Fiers, et al., *Nature* 273: 113 (1978)), or other viral promoters such as those derived from polyoma, Adenovirus 2, bovine papilloma virus, or avian sarcoma viruses. General aspects of mammalian cell host system transformations have been described e.g. by Axel; U.S. Pat. No. 4,399,216. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. Plant cells are now available as hosts, and control sequence compatible with plant cells such as the hopaline synthase promoter and polyadenylation signal sequences (Depicker, A., et al., *J. Mol Appl. Gen* 1: 561 (1982)) are available.

Depending on the host cell used, transformation is done using standard techniques appropriate to such cells. The calcium treatment employing calcium chloride, as described by Cohen, .N., *Proc Natl Acad Sci* (USA) 69: 2110 (1972), or methods described in Molecular Cloning: A Laboratory Manual (1988) Cold Springs Harbor Press, could be used for procaryotes or other cells which contain substantial cell wall barriers. Infection with Agrobacterium tumefaciens (Shaw, C. H., et al., *Gene* 23: 315 (1983)) is believed useful for certain plant cells. For mammalian cells without such cell walls, the calcium phosphate precipitation method of Graham and van der Eb, *Virology* 52: 546 (1978) can be used. Cells may also be transformed in vivo by introducing a gene, incorporated in a vector, directly to cells in the walls of blood vessels using, for example, balloon catheter techniques. WO 90/11734 issued Oct. 18, 1990.

Transformations into yeast can be carried out according to the method of Van Solingen, P., et al., *J Bact* 130:946 (1977) and Hsiao, C. L., et al., *Proc Natl Acad Sci* (USA) 76:3829 (1979).

cDNA or genomic libraries can be screened using the colony hybridization procedure. Generally, each microtiter plate is replicated onto duplicate nitrocellulose filter papers (S&S type BA-85) and colonies are allowed to grow at 37° C. for 14–16 hr on L agar containing 50 μg/ml Amp. The colonies are lysed and DNA fixed to the filter by sequential treatment for 5 min with 500 mM NaOH, 1.5M NaCl, and are washed twice for 5 min each time with 5× standard saline citrate (SSC). Filters are air dried and baked at 80° C. for 2 hr. The duplicate filters are prehybridized at 42° C. for 6–8 hr with 10 ml per filter of DNA hybridization buffer (5× SSC, pH 7.0 5× Denhardt's solution (polyvinylpyrrolidine, plus Ficoll and bovine serum albumin; 1x=0.02% of each), 50 mM sodium phosphate buffer at pH 7.0, 0.02% SDS, 20 μg/ml Poly U, and 50 μg/ml denatured salmon sperm DNA).

The samples can be hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies high temperatures and shorter times are employed. Generally, the filters are washed four times for 30 min each time at 37° C. with 2× SSC, 0.2% SDS and 50 mM sodium phosphate buffer at pH 7, then are washed twice with 2× SSC and 0.2% SDS, air dried, and are autoradiographed at −70° C. for 2 to 3 days.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage can be performed by treating the DNA with a suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. Incubation times of about one hour to two hours at about 37° C. are workable, although variations can be tolerated. After each incubation, protein can be removed by extraction with phenol/chloroform, and may be followed by ether extraction, and the nucleic acid recovered from aqueous fractions by precipitation with ethanol followed by running over a Sephadex G-5 spin column. If desired, size separation of the cleaved fragments may be performed by polyacrylamide gel or agarose gel electrophoresis using standard techniques. A general description of size separations can be found in *Methods in Enzymology* (1980) 65: 499–560.

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides can be prepared by the triester method of Metteucci, et al. *J Am Chem Soc* 103:3185 (1981)) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5mM dithiothreitol, 1–2 Mm ATP, 1.7 pmoles $\gamma^{32}$P-ATP (2.9 mCi/mmole), 0.1 mM spermidine, 0.1 mM EDTA.

Ligations can be performed in 15–30 μl volumes under the following standard conditions and temperatures: 20 mM Tris-Cl pH 7.5, 10mM $MgCl_2$, 10mM DTT, 33 μg/ml GSA, 10mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 mM total end concentration). Intermolecular blunt end ligations (usually employing a 10–30 fold molar excess of linkers) are performed at 1 μM total ends concentration.

In vector construction employing "vector fragments", the vector fragment can be treated with bacterial alkaline phosphatase (BAP) in order to remove the 5' phosphate and prevent religation of the vector. BAP digestions can be conducted at pH 8 in approximately 150 mM Tris, in the presence of Na+ and $Mg+^2$ using about 1 unit of BAP per μg of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis can be used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques can be hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art. Plasmids from the transformants can then be prepared according to the method of Clewell, D. B., et al. *Proc Natl Acad Sci* (USA) 62: 1159 (1969), optionally following chloramphenicol amplification (Clewell, D. B., *J. Bacteriol* 110: 6670 (1972). The isolated DNA is analyzed by restriction and/or sequenced by the dideoxy method of Sanger, F., et al. *Proc Natl Acad Sci* (USA) 74: 5463 (1977) as further described by Messing, et al., *F. Supp. Nucleic Acids Res* 9: 309 (1981), or by the method of Maxam, et al., *Methods in Enzymology* 65: 499 (1980).

For use as an antimicrobial or anti-inflammatory agent, gastrointestinal defensin peptides can be formulated into pharmacological compositions containing an effective amount of gastrointestinal defensin peptide and a usual nontoxic carrier, such carriers being known in the art. The compositions can be given via a route of administration suited to the form of the composition. Such compositions are, for example, in the form of usual liquid preparations including solutions, suspensions, emulsions and the like which can be given orally, intravenously, subcutaneously or intramuscularly. The composition can be administered in an antimicrobially or anti-inflammatory effective amount, which will depend upon the patient, age, weight, and condition.

Additionally, for treatment of microbial infection or gastrointestinal inflammation, endogenous expression of gastrointestinal defensin peptides may be induced in cells. The endogenous production of gastrointestinal defensin peptide may be modulated by contacting cells which express the peptides with a substance which regulates a gene coding for a gastrointestinal defensin peptide. In particular, substances which bind to or otherwise modulate the ordinary transcription of DNA coding for gastrointestinal defensin peptide or which bind to or otherwise inhibit the translation of mRNA coding for gastrointestinal defensin peptide are useful to modulate gastrointestinal defensin production. Methods of identifying or designing effective substances, such as polypeptides, are known to those skilled in the art. Preferably such substances bind to at least a portion of one of the nucleic acid sequence defined in SEQ ID NO: 1, SEQ ID NO: 4 and/or SEQ ID NO: 6. More preferably a substance such as a polypeptide binds to a cis- acting control element of SEQ ID NO: 1.

Alternatively cells selected for expression of gastrointestinal defensin peptides may be transformed in vitro or in vivo with DNA comprising a portion of a gastrointestinal defensin peptide cDNA or genomic sequence as discussed previously. Cells which are transformed in vitro may be introduced into a mammal by methods familiar to those skilled in the art such as by performance of cellular grafts. In vivo transformation may also be accomplished by introduction of a recombinant vector described previously. WO 90/11734 issued Oct. 18, 1990.

It is believed that the gastrointestinal defensin peptides may regulate the level of luminal microbiological flora. The high density of Paneth cells near the distal ileum might contribute to a barrier restricting the abundance of intestinal microbiological flora to the colon. Second, the gastrointestinal defensin peptides may be important in mucosal defense from microbial invasion. An effective host defense system in the small bowel not requiring significant inflammation would preserve of the integrity of the villus epithelium, and thereby maintain the critical function of absorbing nutrients. Gastrointestinal defensin peptides may contribute to such a defense. In some cases, however, too little gastrointestinal defensin peptide is present in the intestinal tract, leading to microbial infection, irritation and inflammation of the epithelium. In other cases, too much gastrointestinal defensin peptide may be inappropriately produced in response to real or artificial stimuli. The epithelium of the gastrointestinal tract may become inflamed in response to the overproduction of defensin peptide. Thus, conditions such as diarrhea, inflammatory bowel disease, necrotizing enterocolitis and gastric ulcer disease may result from underproduction or overproduction of these gastrointestinal defensin peptides. Diseased and abnormal conditions of the gastrointestinal tract may be diagnosed by measuring the amount of defensin peptide or mRNA coding for defensin peptides present in a sample taken from a mammalian gastrointestinal tract and comparing the amount of peptide or mRNA present in the sample with the amount of peptide or mRNA present in a normal mammalian gastrointestinal tract. An abnormal amount of defensin peptide or mRNA coding for defensin peptides is indicative of the likelihood of gastrointestinal disorders such as microbial infection or inflammation.

Furthermore, the susceptibility of a patient to a gastrointestinal disorder such as diarrhea, inflammatory bowel disease, necrotizing enterocolitis, and gastric ulcer disease can be predicted by methods of the present invention. These methods comprise the step of providing a DNA containing test sample from said human patient. Appropriate test samples such as blood or tissue samples are well known to those in the art. DNA from the DNA containing test sample may be amplified using an upstream probe having a sequence complementary to an upstream portion of a selected defensin sequence such as the sequences defined in SEQ ID NO: 1, SEQ ID NO: 4 or SEQ ID NO: 5. and a downstream probe which is complementary to a downstream portion of the selected defensin sequence by methods known in the art such as by polymerase chain reaction (PCR), described in U.S. Pat. No. 4,386,202 issued to Mullis. In some preferred embodiments of the present invention an upstream probe having a sequence as defined in SEQ ID NO: 48 and a downstream probe having a sequence as defined in SEQ ID NO: 39 are used. The term "upstream" is meant to refer to the position of DNA regions relative to the 5' or 3' end of a nucleic acid sequence. Those regions on the 5' side are said to be upstream by those skilled in the art. Likewise, downstream is meant to refer to the position of DNA regions at the 3' end of a nucleic acid sequence. Complementary, as the term is used herein refers to the stable duplex formation resulting from Watson-Crick base pairing. It should be understood by one skilled in the art that some parameters, such as probe length, may vary depending upon the method of amplification selected, however determination of optimal conditions is within the skill of a practitioner. Thereafter amplified DNA may be compared with DNA from a normal sample by any of a range of methods known in the art to identify one or more mutations of the amplified DNA as compared to normal DNA whereby a mutation is indicative of the likelihood that the patient has increased susceptibility to gastrointestinal disorders. A mutation can be any deviation of the nucleic acid sequence which is not present in a normal, or wild type nucleic acid defensin sequence such as a base substitution, base deletion or base addition.

In one embodiment of the present invention, a detectably labeled nucleic acid probe may be contacted with the test sample or amplified DNA from the test sample under hybridizing conditions. The probe should be designed to be substantially complementary to wild type defensin sequences, particularly in regions known or suspected to carry common mutations associated with increased susceptibility to gastrointestinal disorders. For example, probes may be substantially complementary to at least a portion of a defensin sequence as defined in SEQ ID NO:1, SEQ ID NO: 4 and SEQ ID NO:5. Hybridization of detectably labeled probes and the test sample occurs under hybridization conditions which will be apparent to those skilled in the art. For example, hybridization can be performed at 42° C. with 50% formamide, 0.1× SSC, 0.1% SDS, 3× SSC, 1% SDS, 5% dextran sulfate, denatured herring sperm DNA (100 μg/ml). Alternatively hybridization may be performed at 65° C. with 1% SDS, 1M NaCl and 10% dextran sulfate. The parameters of these conditions can of course be modified to optimize hybridization as will be apparent to one skilled in the art. Detectably labeled probes which are substantially complementary to a selected wild type defensin sequence will hybridize to the wild type defensin sequence under hybridizing conditions and a signal will be detected. However, no signal will be detected in the absence of hybridization. The absence of hybridization is diagnostic of the likelihood that the defensin gene carries a mutations and the increased likelihood that the patient may be susceptible to gastrointestinal disorders.

Still other methods which may be used to compare amplified DNA with normal DNA in order to diagnose the susceptibility of a patient to gastrointestinal disorders include direct sequencing such as by modification of methods described by Gyllensten and Erlich, *Proc. Natl. Acad. Science* U.S.A. 85: 7652–7656 (1988); Innis, et al. *Proc. Natl. Acad. Sci.* U.S.A. 85: 9436–9440 (1988); McBride, et al., *Clinical Chem.* 35: 2196–2201 (1989); Ohara, et al., *Proc. Natl. Acad. Sci.* U.S.A. 86: 5673–5677 (1989); Nakamaye, et al., et al. *Proc. Natl. Acad. Sci.* U.S.A. 16: 9947–9959 (1988); Stoflet, et al., *Science* 239: 491–494 (1988) and Schowalter, et al., *Genomics* 6: 23–32 (1990). Multiplex PCR may also be useful for such diagnosis in accordance with methods such as those described in Chamberlain, et al., *Nucleic Acids Research* 16: 11141–11156 (1988) and Chamberlain, et al., *PCR Protocols: A Guide to Methods and Applications* (Academic Press, Orlando, Fla. 1990) pp. 272–281. Mutations of the DNA of a patient may also be detected by subjecting amplified DNA/normal DNA heteroduplexes to enzymatic cleavage such as RNase A cleavage, Myers, et al. *Science* 230: 1242–1246 (1985), or chemical cleavage such as by hydroxylamine and osmium tetroxide (HOT), Cotton, et al., *Proc. Natl. Acad. Sci.* U.S.A. 85: 4397–4401 (1988). Additional methods which may be used to detect mutations in a patient's defensin DNA sequence include denaturing gradient gel electrophoresis (DGGE), Myers, *Nature* 313: 495–498 (1985) and temperature-gradient gel electrophoresis, Rosenbaum and Riesner, *Biophys. Chem.* 26: 235–246 (1987) and Riesner, et al. *Electrophoresis* 10: 377–389 (1989). Additional methods are discussed, for example, by Rossiter and Caskey, *J. Biol. Chem.* 268(22): 12753–12756 (1990).

EXAMPLES

All reagents were reagent grade from Sigma Chemicals (St. Louis, Mo.) unless otherwise noted. Restriction enzymes were purchased from Bethesda Research Laboratories (Gaithersburg, Md.) or Boeringer Mannheim (Indianapolis, Ind.). Oligonucleotides were made by the Nucleic Acid and Protein Core Facility, Department of Pediatrics, University of Pennsylvania School of Medicine. Oligonucleotide probes were end labelled to a specific activity of ca. $10^7$ DPM/pmol using γ-[$^{32}$P] ATP (300 Ci/mmol, DuPont, Wilmington, Del.) and T4 polynucleotide kinase (Stratagene, La Jolla, Calif.). Double-stranded DNA probes were labelled to a specific activity of ca. $10^9$ DPM/μg using α-[$^{32}$P]dCTP (800 Ci/mmol, DuPont) and T7 DNA polymerase (U.S. Biochemicals, Cleveland, Ohio), or using a thermal cycling method with fluorescently labelled primer oligonucleotides and Taq DNA polymerase (Applied Biochemical Systems, Foster City, Calif.). PCR products, purified by glass milk adsorption (Bio101, La Jolla, Calif.) were incubated in a standard fill-in reaction with T4 DNA polymerase (Pharmacia, Piscataway, N.J.) and then subcloned by ligation to linearized, blunt-end plasmid DNA (Bluescript, Statagene). Sequence data were analyzed using the DNA and protein analysis software MacVector (IBI, New Haven, Conn.).

Example 1

Probe construction

The nucleotides encoding the signal sequence of rabbit defensin 1 and 2 (Ganz et al., *J Immunol* 143: 1359–1365 (1989) are 95% identical to that of human defensin 1 and 3(54/57 identical nucleotides, FIG. 1) (Daher et al., *Proc Natl Acad Sci* USA 85: 7327–7331 (1988); Mars et al., *Blood* 71: 1713–19 (1988); Wiedemann et al., *Leukemia* 3: 227–234 (1989). The nucleotide identity drops in other regions, remaining low over the segment encoding the mature peptides (53% nucleotide identity). The overall identity between these two cDNA sequences averages about 62%. We designed a 43-base oligonucleotide having the sequence CTTGCTGCCATTCTCCTGGTGGCCCTGCAGGCCCAGGCTGAGC (D5'oligo; SEQ ID NO: 35) based on the sequence within the region of identity (FIG. 1). We also constructed a double stranded probe (CB587) which spans residues −29 to +184 (numbering relative to the first nucleotide of the putative initiating codon) of the human defensin 1 cDNA (Daher et al., *Proc Natl Acad Sci* USA 85: 7327–7331 (1988). About half of the DNA sequence of CB587 consists of the region of high conservation, the other half is more specific to human defensin 1 and 3. A search of the Gen-Bank data base (release 60.0) using the University of Wisconsin Genetics analysis software (Devereux et al., *Nucl Acids Res* 12: 387–395 (1984) found no sequences with significant similarity to these probes other than the known defensins.

In addition the following probes were constructed: HNP19s (5' untranslated region): CCCTGCCTAGCTAGAGGATTT (SEQ ID NO: 49), HNP367a:(3' untranslated region) TTCCCTGTAGCTCTCAAAGCAAAT (SEQ ID NO: 37), and HNP317s: (coding region) GAGACCCGTAAGACGACGACT (SEQ ID NO: 36).

Probes were constructed on an automated DNA synthesizer (Applied Biosystems Model 380B).

Example 2

Southern Blot Analysis of DNA digests to detect defensin family diversity

Genomic DNA was digested to completion with restriction enzymes according to the recommendation of the supplier. DNA samples were sized fractionated by agarose gel electrophoresis, and blotted to nylon membranes using standard techniques (Reed and Mann, *Nucl Acids Res* 13: 7207–7221 (1985); Sambrook, et al., Molecular cloning: *a laboratory manual* Cold Spring Harbor, Cold Spring Harbor Laboratory Press (1989). Hybridization with the [$^{32}$P]-5' end-labelled oligonucleotide probes D5'oligo (SEQ ID NO: 35), HNP19s (SEQ ID NO: 49), HNP367a (SEQ ID NO: 37) and HNP317s (SEQ ID NO: 36) was in 20% formamide, 5× SSC, 1× Denhardt's and 1% SDS at 42° C. The double-stranded probes CB587 and pSI25-3'Mbo2 were labelled by random primer synthesis and hybridized in 25% (CB587) or 50% (pSI25-3'Mbo2) formamide, 5× SSC, 1× X Denhardt's and 1% SDS at 42° C. The blots were washed for 1 hour at room temperature in 2× SSC and then in 2× SSC for 30 minutes at a higher temperature of 55° C. (HNP19s, HNP367a, HNP317s), 58° C. (CB587; SEQ ID NO: 38), 60° C. (D5'oligo) or 63° C. (D5'oligo). The final high stringency wash for the blot hybridized with pSI25-3'Mbo2 was in 0.1× SSC at 65° C. for 30 minutes. The moist filters were then subjected to autoradiography at −70° C. in the presence of a Cronex Lightening Plus intensifying screen (DuPont). Blots were stripped of probe by incubating in 0.5M NaOH/1.5M NaCl at room temperature for 20 to 40 minutes, neutralized and then exposed to film to document removal of prior signal.

In a Southern blot of the human DNA digest probed with D5'oligo multiple hybridization bands of similar intensity were observed in each of 4 lanes, and hybridization to high molecular weight DNA was observed for samples digested with Sal-1 and Xho-1. The activity of these two enzymes is sensitive to the methylation status of DNA, suggesting that the probe is hybridizing to a DNA region that is highly methylated in this sample. Comparable results are seen when the final wash condition was 2× SSC at 63° C. Qualitatively similar results were also observed when the blot was sequentially stripped of probe and rehybridized with CB587 or HNP19s. In contrast to these observations, hybridization of the same blot to the HNP367a probe, corresponding to sequences in the 3'-untranslated region of human defensin 1 and 3 cDNAs yielded single bands in these restriction digestions under similar conditions of stringency. Single bands of hybridization were seen with the HNP317s probe from a portion of the condign region of human defensin 1 and 3 cDNA. These latter control experiments indicated that the conditions of stringency used in this series of experiments were adequate to identify highly complementary sequences in genomic DNA. In a Southern blot of DNA from each of 7 species of animals digested to completion with HindIII, and probed with CB587 several strong bands were seen in both human and monkey samples, and weaker bands were seen in all of the other species. Very weak bands were seen in the mouse lane. The results indicate that human DNA contains numerous sequences with significant similarity to a conserved portion of defensin mRNA, and the conservation of sequence extends between species. The conditions used were 25% formamide/5× SSC at 42° C. for the hybridization and 58° C. in 2× SSC for the final wash.

Example 3

Screening of an Unamplified Human Genomic Library

Lifts were made using Colony/Plaque Screen filters (DuPont), and the filters were screened using standard techniques (Sambrook et al., Molecular cloning: *a laboratory manual* Cold Spring Harbor, Cold Spring Harbor Laboratory Press (1989). The standard conditions for annealing and washing (Sambrook et al., Molecular cloning: *a laboratory manual* Cold Spring Harbor, Cold Spring Harbor Laboratory Press (1989) were modified: 42° C., 20% formamide/5× SSC for hybridization and 55° C., 2× SSC for high stringency wash. Plaques were taken through 3–4 rounds of purification at progressively lower densities. Phage DNA was isolated using Lambda-sorb (Promega, Madison, Wis.). Phage insert DNA was subcloned by ligation into the multiple cloning site of Bluescript plasmid DNA. Nested deletions of plasmid insert DNA for sequence analysis were created using an exonuclease III/mung bean nuclease reagent kit (Stratagene) according to the protocol of the supplier. All reported sequences were obtained from both strands of DNA.

An unamplified human genomic library (kindly provided by Drs. M. Budarf and B. Emanuel (McDermid et al., *Genomics* 5: 1–8 (1989)) was screened with D5'oligo as described in Example 2. From approximately four genome equivalents of individual clones at a density of $2\times10^4$/150mm plate, 35 relatively strong signals were obtained on single filters. Twenty signals were taken to secondary screen and twelve of these signals remained positive and were plaque-purified. The twelve clones were categorized by a combination of restriction enzyme, hybridization and partial sequence analysis. All twelve genomic clones had inserts in the range of 12–15 kB and many contained more than one restriction fragment which contained a defensin-related sequence. Hybridization properties to a panel of oligonucleotides and partial sequence analysis indicated that five of these clones contained sequences consistent with genes corresponding to bone marrow derived defensins 1 and 3. These clones were temporarily set aside. Partial characterization of several other clones reveals that they also contained defensin sequences. One clone, HG-2 was selected for in-depth characterization. An EcoR1 restriction fragment that contained the defensin-like sequence within this clone was isolated and the nucleotide sequence was determined (FIG. 2). Sequence analysis revealed two open reading frames that appear to encode portions of a putative preprodefensin molecule.

Example 4

PCR Amplification to determine tissue expression of defensin genes

Figure 3A:
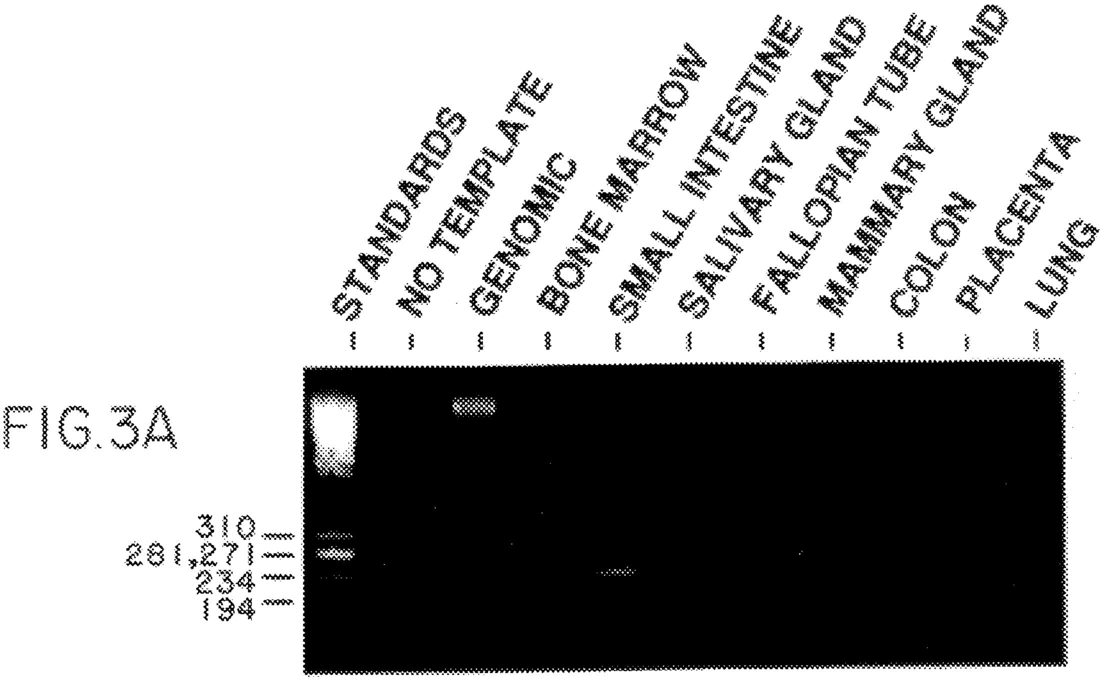
FIG. 3A shows the results of a PCR reaction using cDNA from eight tissues and genomic DNA as templates. Two primers used in the PCR reaction were chosen from potential open reading frames (ORF) of the genomic sequence. HNP63s was a sense oligonucleotide from the upstream ORF, and HSIA261a was an antisense oligonucleotide from the downstream ORF. Pools of lambda phage cDNA from respective human tissues were used as PCR templates. Included as a control was human genomic DNA as a template. A standard protocol for amplification was used. Amplification products were size fractionated in a 3% agarose gel. A band of ca. 1.2 kB was seen in the genomic DNA sample, consistent with amplification across the intron. A band of 230 nucleotides was seen in the small intestine sample. No bands were seen in the other cDNA samples.

PCR amplification was carried out using standard protocols as described (Saiki et al., *Science* 239: 487–491 (1988). Initial denaturation was at 94° C.; 35 cycles of amplification were done by cycling one minute at 94° C., one minute at 55° C. and two minutes at 72° C. Pools of cDNA for use as PCR templates were prepared from plate lysates contain 3–5 $\times10^5$ phage. All human cDNA libraries used are commercially available (Clontech), except from the small intestine which was obtained as a gift from L. Chan, Baylor University School of Medicine. For amplification of defensin 5 related sequences an upstream sense primer was chosen from one defensin-related open reading frame (HNP63S: TCGCCATCCTTGCTGCCATT; SEQ ID NO: 48) and the downstream antisense primer was from the other (HSI261a: CGGCCACTGATTTCACACAC; SEQ ID NO: 39). These primers were chosen so the amplification product would include an intron when the template was genomic DNA, a possible contaminant in a pool of cDNA. FIG. 3A shows the results of a PCR reaction using cDNA from eight tissues and genomic DNA as templates. A band of ca. 1.2 kB was seen in the genomic DNA sample, consistent with amplification across the intron. A band of 230 nucleotides was seen in the small intestine sample. No bands were seen in the other cDNA samples. Similar results were seen after amplification of defensin 6 related sequences.

Figure 3B:
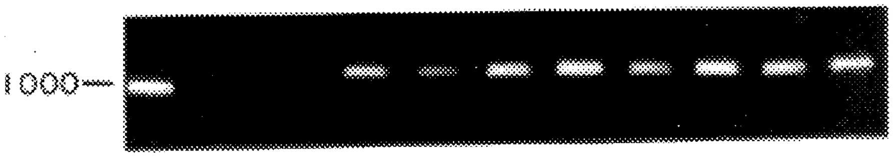
FIG. 3B shows a control amplification using alpha-tubulin primer pairs HTUBs and HTUBa to demonstrate the presence of adequate cDNA template from all tissues.

Control amplifications from the cDNA templates used primer pairs (HTUBs: GATTGGCAATGCCTGCTGGGA; SEQ ID NO: 40 and HTUBa: CAGGTTGGTCTGGAATTCTGT; SEQ ID NO: 42) from the alpha-tubulin sequence (Cowan et al., *Mol Cell Biol* 3: 1738–1745 (1983). This amplification showed that all cDNA samples contained amplifiable template. (FIG. 3B).

Figure 3C:
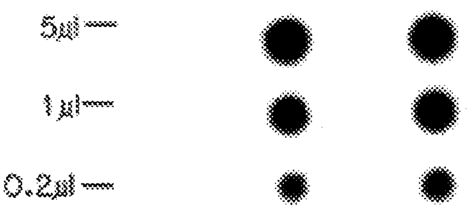
FIG. 3C is a filter hybridization of the amplification products from 3A with a probe (pSI25-3'Mbo2) consisting of nucleotides 121 to +450 of the defensin 5 cDNA under conditions of high stringency (final wash 65° C., 0.1× SSC, overnight exposure).

Subsequent hybridization of the amplification product to the pSI25-3'Mbo2 probe spanning most of the putative exon 2 under high stringency confirmed the authenticity of the amplified DNA, and suggested high relative abundance of this sequence in the small intestine cDNA pool. (FIG. 3C). On longer exposure there is some signal in fallopian tube and placenta. Similar results were observed for defensin 6. A second control experiment using similarly designed primer pairs from the sequence of the human and defensin 1 and 3 cDNA yielded strong ethidium bromide staining band from the bone marrow cDNA and genomic DNA templates, but not from the small intestine or other cDNAs.

Example 5 cDNA Cloning

Figure 4A:
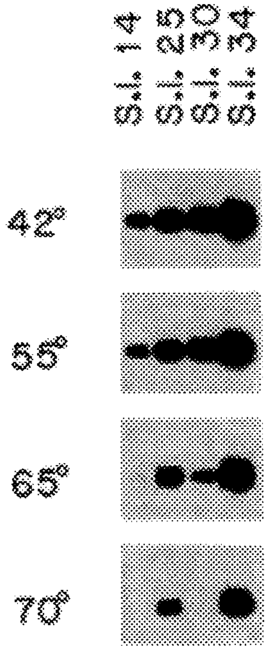
FIG. 4A is a Southern blot hybridization of 4 lambda gt11 phage inserts isolated from a human small intestine cDNA library probed with D5' oligo. Final washes in 2× SSC were at the indicated temperatures.
Figure 4D:
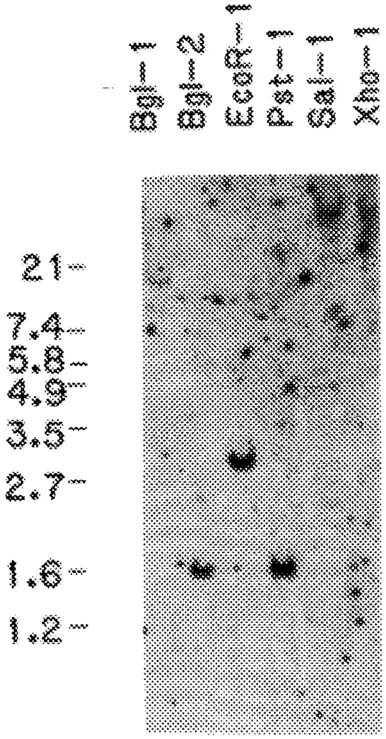
FIG. 4D is a Southern blot hybridization of human genomic DNA probed with pSI25-3'Mbo2, a segment of human defensin 5 cDNA 3' to the Mbo2 site (nucleotides +121 to +450). The filter was the same as that used in FIG. 2B following stripping of the probe. Hybridization was in 50% formamide/5× SSC at 42° C., and the high stringency wash was in 0.1× SSC at 65° C. for 30 minutes. The autoradiographic exposure was 14 days.

We screened 2.5×105 lambda cDNA clones of a human small intestine library with D5'oligo (Chen et al., *Science* 238: 363–366 (1987) (generous gift of Dr. Lawrence Chan, Baylor Univ.). We observed 40 duplicate signals on primary screening. Twelve clones were taken through three rounds of plaque purification and isolation of phage DNA. Ten of these clones hybridized strongly with probes D5'oligo and CB587, and within these ten, two classes of clones were evident from hybridization patterns. FIG. 4A shows the hybridization pattern seen for two clones representative of each class when probed with D5'oligo and then washed at progressively higher temperature. The inserts from these four clones were subcloned and sequenced completely in both directions. Sequence analysis indicated clone 34 was identical to clone 25 except that it extended 9 bases further at the 5' terminus (to nucleotide −19), and clone 14 overlapped clone 30 in a similar fashion. FIG. 4B shows the sequence alignment of each class of small intestine clones with the probe, D5'oligo. Clones 1 and 2 had sequence which corresponded exactly to the oligonucleotide probe; clones 3 and 4 were 85% identical. Both of these two classes of clones have an open reading frame, and the deduced amino acid sequence indicates that each encodes a novel putative preprodefensin. Further hybridization experiments using probes from the 3' portion of these clones demonstrates that the heterogeneity amongst these 10 isolated cDNA clones appears to be limited to two classes.

Example 6

RACE-PCR

To obtain additional nucleotide sequence of the 5'-segment of this message, a pool of small intestine cDNA was amplified using the rapid amplification of cDNA ends (RACE) technique. The RACE-PCR protocol was modified from Frohman (Frohman et al., *Proc Natl Acad Sci* (USA) 85: 8998–9002 (1988). Total RNA (10 μg) and a poly-dT primer (In Vitrogen, San Diego, Calif.) was used in the reverse transcription step. The DNA product was tailed with dATP and terminal transferase. This DNA product was then used as a template in a PCR using the T7RACE (TACGACTCACTATAGTTTTTTTTTTTTTTT; SEQ ID NO: 43) primer-linker sequence as an upstream primer, a commercially available T7 oligonucleotide (AATACGACTCACTATAG; SEQ ID NO: 44) and a downstream primer, HSI220a (GGACTCACGGGTAGCACAAC; SEQ ID NO: 45), an antisense oligonucleotide from the putative coding region of the cDNA, as PCR primers according to the method described (Frohman et al., *Proc. Natl Acad Sci* (USA) 85: 8998–9002 (1988). A diffuse band of approximately 270 nucleotides was detectable by ethidium bromide staining (data not shown). The amplification product was subcloned into a plasmid vector and three clones that extended to the methionine codon were analyzed. One of the clones extended from the downstream primer and terminated at nucleotide −10, and may represent premature termination of the reverse transcriptase. The sequence of the other two clones were identical, with extension from the downstream primer to nucleotide −40. The nucleotides +172 through −40 in this primer extension product correspond to contiguous nucleotides 1570–1359 in the genomic sequence of HG-2 (FIG. 2). The composite cDNA sequence from these overlapping clones is presented in FIG. 4C, with nucleotides obtained from the PACE-PCR studies underlined. The sequence has an open reading frame of 282 nucleotides which encodes a defensin-like prepropeptide. The 3' unique portion of this cDNA detects single bands of hybridization in Southern Blot analysis (FIG. 4D), consistent with a signal copy of this gene in the human genome.

Example 7

Northern Blot Analysis

RNA samples from small intestine and several other human tissues were subjected to northern blot analysis using an oligonucleotide probe from this cDNA sequence (HSIA309a) FIG. 5. Total RNA (Clontech, Palo Alto, Calif.) was fractionated by agarose gel electrophoresis in the presence of formaldehyde and blotted to nylon membranes (Zetabind, Cuno, Inc., Meriden, Conn.) by the capillary technique (Sambrook et al., Molecular cloning: *a laboratory manual* Cold Spring Harbor, Cold Spring Harbor Laboratory Press (1989). RNA size standards (BRL) were run in parallel lanes. The filter containing poly-A enriched RNA was similarly prepared (Clontech). Radioactively labelled DNA probes were hybridized to the immobilized RNA in 50% (v/v) formamide/5× SSC/5× Denhardt's/1% (w/v) SDS at 37° C., and washed in 1× SSC/0.1% SDS at 55° C., the same conditions of stringency as used in the in situ hybridization protocol (see below). The oligonucleotide probes used in these experiments were: SIG68A (GAGTGGCTCAGCCTGGGCCTGCAGGGCCACCAGG AGAATGG CAGCAAG; SEQ ID NO: 41), HSIA262s (CTCTACAGACTCTGCTGTC GCTGAGCTTCCTAGATAGAAACCAAAGCA; SEQ ID NO: 46) and HSIA309a (TGCTTTGGTTTCTATCTAGGAAGCTCAG CGACAGCAGAGTCTGTAGAG; SEQ ID NO: 47). Autoradiographic exposure time at −70° C. with an intensifying screen was 2–14 days. Blots were stripped of oligonucleotide probe by incubation in 0.1× SSC/0.1% SDS at 65° C., and then re-exposed to film to document removal of prior signal. The HSIA309a probe recognized an abundant message of approximately 600 nucleotides in the small intestinal RNA (FIG. 5A, 10 μg total RNA, 3 day exposure). Similar results were observed for defensin 6 probes. Under the same experimental conditions, no message was detected in pancreas, kidney, skeletal muscle, liver, lung, placenta, brain or heart samples (FIG. 5B, 2 μg poly-A RNA, 10 day exposure), despite the presence of intact RNA in these lanes as demonstrated by hybridization to a beta-actin probe (FIG. 5C). Again, similar results were observed for defensin 6. A control experiment using a signal sequence oligonucleotide showed a defensin-related mRNA in the lung sample under very similar conditions of stringency (FIG. 5D). A much fainter signal at this position (approximately 550 nucleotides) of migration was also detected in the placenta sample. The presence of a defensin related sequence in human lung tissue is consistent with prior northern blot analysis using a probe for defensin 1 and 3 (Daher et al., *Proc Natl Acad Sci* USA 85:7327–7331 (1988), recent protein data from fetal lung tissue (Bateman et al., *J Biol Chem* 266:7524–7530 (1991) and investigations in our laboratory which led to the cloning of HNP-1 cDNA from a human lung library.

Example 8

In situ Hybridization

The cellular localization of the defensin message was determined by in situ hybridization. Tissue sections of adult human intestinal mucosa were probed with sense and antisense $^{35}$S-labelled oligonucleotides. Strong signal was observed with the antisense oligonucleotide probe, HSIA309a in epithelial cells at the base of small intestinal crypts in sections from the adult ileum. No signal was observed in parallel sections if the sense oligonucleotide probe, HSIA262s was used or if the sections were first treated with ribonuclease prior to hybridization with HSIA308a. Control experiments demonstrated that both the sense and antisense oligonucleotides were equally effective at hybridizing to pSI25-3'Mbo2 double stranded plasmid DNA under these experimental conditions. Crypt cells with similar if not identical morphological characteristics stained strongly with phloxine-tartrazine, a histochemical stain commonly used to detect Paneth cells (Lendrum, *J Pathol Bacteriol* 59:399–404 (1947). Eosinophils present in the lamina propria of numerous small intestinal sections also appeared to be weakly positive with the antisense oligonucleotide probe used in these experiments, however the signal was not attenuated with pre-treatment with RNase and the sense oligonucleotide appeared equally positive (data not shown). The simplest explanation from these control experiments is that the signal in these white cells is probably artifactual and not from hybridization to cellular RNA. No other cells in these sections hybridized to any of the probes.

Example 9

Antimicrobial activity of Defensin 5

Purified defensin 5 is tested on several strains of bacteria including *Escherichia coli, Staphylococcus aureus, Pseudomonas aeruginosa* and *Candida albicans* to determine its antimicrobial activity in vitro. Minimal inhibitory concentrations are determined by incubating approximately 2.5 ×10$^4$ microbe in 0.25× TSB with 50, 25, 12.5, 6.25 or 3.125 μg/ml of the peptide. The minimal inhibitory concentration (μg/ml) should be approximately 3.125 μg/ml.

What is claimed is:

1. A contact disinfectant comprising an antimicrobially effective amount of a gastrointestinal defensin peptide having an amino acid sequence set forth in SEQ ID NO: 5.

2. A contact disinfectant comprising an antimicrobially effective amount of a gastrointestinal defensin peptide having an amino acid sequence set forth in SEQ ID NO: 7.

3. A substantially pure gastrointestinal defensin peptide having the amino acid sequence set forth in SEQ ID NO: 5.

4. A substantially pure gastrointestinal defensin peptide having the amino acid sequence set forth in SEQ ID NO: 7.

5. A non-naturally occurring recombinant vector that is expressed in a suitable expression system comprising a DNA sequence encoding a gastrointestinal defensin peptide having the amino acid sequence set forth in SEQ ID NO: 5.

6. A non-naturally occurring recombinant vector that is expressed in a suitable expression system comprising a DNA sequence encoding a gastrointestinal defensin peptide having the amino acid sequence set forth in SEQ ID NO: 7.

7. The vector of claim 5 wherein the DNA sequence is the sequence defined by SEQ ID NO: 4.

8. The vector of claim 5 wherein the DNA sequence is the sequence defined by SEQ ID NO: 6.

* * * * *

UNITED STATES PATENT AND TRADEMARK OFFICE

CERTIFICATE OF CORRECTION

PATENT NO. : 5,641,497

DATED : June 24, 1997

INVENTOR(S) : Charles L. Bevins and Douglas E. Jones

It is certified that error appears in the above-identified patent and that said Letters Patent is hereby corrected as shown below:

Col. 5, line 65, before "121" insert --+--

Col. 9, line 31, "cystsine" should be --cysteine--.

Col. 9, line 32, "cystsine" should be --cysteine--.

Col. 21, line 63, after "signal." start the next sentence with a paragraph.

Signed and Sealed this

Twenty-fifth Day of November, 1997

Attest:

BRUCE LEHMAN

*Attesting Officer* *Commissioner of Patents and Trademarks*

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
( A ) LENGTH: 2880 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 1399..1572

( i x ) FEATURE:
( A ) NAME/KEY: CDS
( B ) LOCATION: 2552..2663

( i x ) FEATURE:
( A ) NAME/KEY: TATA_signal
( B ) LOCATION: 1328..1334

( i x ) FEATURE:
( A ) NAME/KEY: CAAT_signal
( B ) LOCATION: 1267..1271

( i x ) FEATURE:
( A ) NAME/KEY: misc_signal
( B ) LOCATION: 1569..1576

( i x ) FEATURE:
( A ) NAME/KEY: misc_signal
( B ) LOCATION: 2539..2549

( i x ) FEATURE:
( A ) NAME/KEY: polyA_signal
( B ) LOCATION: 2770..2775

( x i ) SEQUENCE DESCRIPTION: SEQ ID NO:1:

```
CAAATATAGA GACTCTCCAA GGGCCCACTG AGCCCCAAAG GATTTGGATC AAATATGGTG     60
ATATTATGGA AATATGTAGT AATATCTTAA AAATGTGTAA GATATAGTCT CTTTTTTTTT    120
TTTTTTAAGA GAAGGGGTCT CACTATGTTT TTAGGCTGGT ATCGAACTCC TGGTCTCCAG    180
TGATCCTCCC ACCTCAGCCT GTCAAATAGC TAGAAATATA GGCATGTACC ACCATGCTGG    240
CTTAAGATGC ATTCTTTGAC ACAGCAATTC TATTTCTATA AGTTTATCCA TATAGGTAAG    300
AGAACATATA TACAAGATAA TCACTGTAAC TTTACTTATT ACTGCAAAAG TTTAAAAATA    360
ACCAAATTGT AATAATTTTA TAATATTTTA TCAGTACAAA AAATAAGTGA TGGCATATAC    420
AAACCCTGGG ATAGTATAAG GCTATTAAAA TTATAATAGC ATTCCATGTA TTTTGATATA    480
CAAAGTGCCA ATGTTACAGG TGAAAAAAGC GAAGTGCAGA ATACTATGTG TAACTGTTAA    540
TAGTGATGGT TTGCTGGGTC AGAACTGAAG GCCTGGGGGT AGAAATGAGA GCTCATGACT    600
TCTACCTTTT GAATGTTGTT CCTTGTGCAT GATTTACAAT TTTCTAAAAC TAAAAAAAAA    660
ATCTCAGAAA GGGGCTGTAC GCACCTAAAT TACTTTGATA TTCCCCAAAG TGGAGAGAAG    720
TACCCGCTAC ACATTTTATG TGATGCATTC AGATCACACC AACTCCTTGA ACTAAATCCG    780
AATTTTTATT TTAATCTGAT AAACTTGGCC TACTATTTTA CTGAACTCAT TTCCCCTATA    840
GCCTGATAAG GTCATTGACC TCTCCATACT GGCACCAGCG GGAGACTACT CACCTCGAGA    900
TCTCAAAAGC CTCCTACATG AGGTTAGTAA TATCCCTGAA TCCTGCAATG AATTAACTCT    960
```

-continued

CTACTCCACT GGGTCCCAGG TCTGCCCCCA GAGAGTCATC CAGAGAGTAC CAGGGACCAT 1020

CTTCAGAAAA CAAGAGGCAT TTGATCCCCA AACTTCTTGA ATGAAAGCGC TGTTGTTTTT 1080

CTTTTTTGAA TATATAAAAG TAAATACTCA AGCAGATGGG AAACAGAACA GGATAGTAAT 1140

ACCCTTATCA TCATTAACAC CTTGGATCAA GAAGAGGCAT TAAGCATACA GACTCACGCT 1200

TTGATGAAAG CTGGGAGAAA GAGGAGCATC AAAGGGATCT CGAGAACAAA GGCAGTCCTT 1260

CCCCTCCCAA TCACATGCCC ACCTCCTCTC ACTGCAGCTT CTGTCTCAGG TCTTCTCCCA 1320

GCAGAGCTAT AAATCCAGGC TGACTCCTCA CTCCCCACAT ATCCACTCCT GCTCTCCCTC 1380

CTGCAGGTGA CCCCAGCC ATG AGG ACC ATC GCC ATC CTT GCT GCC ATT CTC 1431

Met Arg Thr Ile Ala Ile Leu Ala Ala Ile Leu
1 5 10

CTG GTG GCC CTG CAG GCC CAG GCT GAG TCA CTC CAG GAA AGA GCT GAT 1479
Leu Val Ala Leu Gln Ala Gln Ala Glu Ser Leu Gln Glu Arg Ala Asp
15 20 25

GAG GCT ACA ACC CAG AAG CAG TCT GGG GAA GAC AAC CAG GAC CTT GCT 1527
Glu Ala Thr Thr Gln Lys Gln Ser Gly Glu Asp Asn Gln Asp Leu Ala
30 35 40

ATC TCC TTT GCA GGA AAT GGA CTC TCT GCT CTT AGA ACC TCA GGT 1572
Ile Ser Phe Ala Gly Asn Gly Leu Ser Ala Leu Arg Thr Ser Gly
45 50 55

AGGAGACATC AATCTTGCAC ATCTGCAAAA TCTAGAAAAA AAGGATTGGA GAAAGGATCT 1632

GGAGTCAAGT GTGGAAAGGT CTACCTCACT TGAGTGACTT TACTTAATCT TCCTGGACCT 1692

TGATTTTCTC ATCTATAAAT TAATCAGTGA GAACCAAATA AATCTAAAAG ATTTTCTTTT 1752

TTCTAAGACT TTCAGCTCCA AGATATTTCT GTGAAATTTG CTACTTTTAA GATAGAAAGA 1812

GCTACACTGA CTAGTTCTTT GTAGATCTAA ATGGGCAGAC TTAGTTATAT AGAGAGTGTT 1872

TTACTTTGTC CATTGGAAAA GCTTTTAGAA CCTAGAGAGG AACCTATAGG TGTGTTTTGA 1932

TGTAGGCTAA TAGGCTTGAT TAAATCTTTC TACAATACAT CCTTAGATCA AAACATCATA 1992

TTGTGTCTCA TACATATACA CAATTATTGT TTGTCAATTA AAACAAGTAA ATATGTAAAA 2052

TGTTAAAAAA AAAAAAAAAA AAAAAAGGAG AGACAGAGAA TGAAGAATTT GAATTTGGAA 2112

AGTCTTCAAA GACTCCTTGA GCACCAAAGT ATTTGGTCCA TGACATTAGC ATGCACAATG 2172

CGGCATTTCA GAAACTGATT CAGGTGCTTT AGGGAGCCTT GTTAGGACCT GGAAATCACA 2232

CATGGAGGTC AAGATTAGGC GTGTGGATGA AGCAGAATGA AGAGTAGGTA ACCCTGAGGT 2292

TGAGAGGTAT ATTGTTGGAC CAGGGAGCAG GTAATAAATA CATCCTGGAT AGACTCACAT 2352

GGGGAAAAAA ACTATGATCT TGCATGACTA ACACATAGCT AGTAAGATTT CTTGTCACTT 2412

ACGACAAAGA CATGAATTTT CTCCATCCTA ACATGACTGA TACAGTGTCT CTTATTTAGA 2472

CTATCTCAGT TAGTCTGGCT GTGCTTGTCC TTTTTCCCAC CTCCCTCGCT GTGCCTGACC 2532

CTCTCTTCTT TCCACAGGT TCT CAG GCA AGA GCC ACC TGC TAT TGC CGA ACC 2584

Ser Gln Ala Arg Ala Thr Cys Tyr Cys Arg Thr
1 5 10

GGC CGT TGT GCT ACC CGT GAG TCC CTC TCC GGG GTG TGT GAA ATC AGT 2632
Gly Arg Cys Ala Thr Arg Glu Ser Leu Ser Gly Val Cys Glu Ile Ser
15 20 25

GGC CGC CTC TAC AGA CTC TGC TGT CGC TGAGCTTCCT AGATAGAAAC 2679
Gly Arg Leu Tyr Arg Leu Cys Cys Arg *
30 35

CAAAGCAGTG CAAGATTCAG TTCAAGGTCC TGAAAAAAGA AAAACATTTT ACTCTGTGTA 2739

CCTTGTGTCT TTCTAAATTT CTCTCTCCAA AATAAAGTTC AAGCATTAAA CTTAGTGTGT 2799

-continued

TTGACCTTTT TAATTTTCTT TTCTTTTTCC TTTTTTTTCT TTTGCTTTGT TATATGGTGG 2859

TTTGTATGGT TCCTTTGTAT T 2880

( 2 ) INFORMATION FOR SEQ ID NO:2:

( i ) SEQUENCE CHARACTERISTICS:
( A ) LENGTH: 58 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Arg Thr Ile Ala Ile Leu Ala Ala Ile Leu Leu Val Ala Leu Gln
 1               5                  10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly
    50                  55
```

( 2 ) INFORMATION FOR SEQ ID NO:3:

( i ) SEQUENCE CHARACTERISTICS:
( A ) LENGTH: 36 amino acids
( B ) TYPE: amino acid
( D ) TOPOLOGY: linear ( i i ) MOLECULE TYPE: protein ( x i ) SEQUENCE DESCRIPTION: SEQ ID NO:3:

```
Ser Gln Ala Arg Ala Thr Cys Tyr Cys Arg Thr Gly Arg Cys Ala Thr
 1               5                  10                  15

Arg Glu Ser Leu Ser Gly Val Cys Glu Ile Ser Gly Arg Leu Tyr Arg
            20                  25                  30

Leu Cys Cys Arg
        35
```

( 2 ) INFORMATION FOR SEQ ID NO:4:

( i ) SEQUENCE CHARACTERISTICS:
( A ) LENGTH: 424 base pairs
( B ) TYPE: nucleic acid
( C ) STRANDEDNESS: single
( D ) TOPOLOGY: unknown ( i x ) FEATURE:
( A ) NAME/KEY: CDS
( B ) LOCATION: 10..294

( x i ) SEQUENCE DESCRIPTION: SEQ ID NO:4:

```
ACCCCAGCC ATG AGG ACC ATC GCC ATC CTT GCT GCC ATT CTC CTG GTG      48
          Met Arg Thr Ile Ala Ile Leu Ala Ala Ile Leu Leu Val
           1               5                  10

GCC CTG CAG GCC CAG GCT GAG TCA CTC CAG GAA AGA GCT GAT GAG GCT    96
Ala Leu Gln Ala Gln Ala Glu Ser Leu Gln Glu Arg Ala Asp Glu Ala
    15                  20                  25

ACA ACC CAG AAG CAG TCT GGG GAA GAC AAC CAG GAC CTT GCT ATC TCC   144
Thr Thr Gln Lys Gln Ser Gly Glu Asp Asn Gln Asp Leu Ala Ile Ser
 30                  35                  40                  45

TTT GCA GGA AAT GGA CTC TCT GCT CTT AGA ACC TCA GGT TCT CAG GCA   192
Phe Ala Gly Asn Gly Leu Ser Ala Leu Arg Thr Ser Gly Ser Gln Ala
                50                  55                  60
```

-continued

```
AGA GCC ACC TGC TAT TGC CGA ACC GGC CGT TGT GCT ACC CGT GAG TCC      240
Arg Ala Thr Cys Tyr Cys Arg Thr Gly Arg Cys Ala Thr Arg Glu Ser
            65                  70                  75

CTC TCC GGG GTG TGT GAA ATC AGT GGC CGC CTC TAC AGA CTC TGC TGT      288
Leu Ser Gly Val Cys Glu Ile Ser Gly Arg Leu Tyr Arg Leu Cys Cys
        80                  85                  90

CGC TGAGCTTCCT AGATAGAAAC CAAAGCAGTG CAAGATTCAG TTCAAGGTCC           341
Arg  *
    95

TGAAAAAAGA AAAACATTTT ACTCTGTGTA CCTTGTGTCT TTCTAAATTT CTCTCTCCAA    401

AATAAAGTTC AAGCATTAAA AAA                                            424
```

(2) INFORMATION FOR SEQ ID NO:5:

(i) SEQUENCE CHARACTERISTICS:
(A) LENGTH: 94 amino acids
(B) TYPE: amino acid
(D) TOPOLOGY: linear (ii) MOLECULE TYPE: protein (xi) SEQUENCE DESCRIPTION: SEQ ID NO:5:

```
Met Arg Thr Ile Ala Ile Leu Ala Ala Ile Leu Leu Val Ala Leu Gln
  1               5                  10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
 65                  70                  75                  80

Val Cys Glu Ile Ser Gly Arg Leu Tyr Arg Leu Cys Cys Arg
                85                  90
```

(2) INFORMATION FOR SEQ ID NO:6:

(i) SEQUENCE CHARACTERISTICS:
(A) LENGTH: 452 base pairs
(B) TYPE: nucleic acid
(C) STRANDEDNESS: single
(D) TOPOLOGY: unknown (ix) FEATURE:
(A) NAME/KEY: CDS
(B) LOCATION: 19..321

(xi) SEQUENCE DESCRIPTION: SEQ ID NO:6:

```
CCTCCAGCGA CCCTAGCC ATG AGA ACC CTC ACC ATC CTC ACT GCT GTT CTC       51
                    Met Arg Thr Leu Thr Ile Leu Thr Ala Val Leu
                      1               5                  10

CTC GTG GCC CTC CAG GCC AAG GCT GAG CCA CTC CAA GCT GAG GAT GAT       99
Leu Val Ala Leu Gln Ala Lys Ala Glu Pro Leu Gln Ala Glu Asp Asp
            15                  20                  25

CCA CTG CAG GCA AAA GCT TAT GAG GCT GAT GCC CAG GAG CAG CGT GGG      147
Pro Leu Gln Ala Lys Ala Tyr Glu Ala Asp Ala Gln Glu Gln Arg Gly
        30                  35                  40

GCA AAT GAC CAG GAC TTT GCC GTC TCC TTT GCA GAG GAT GCA AGC TCA      195
Ala Asn Asp Gln Asp Phe Ala Val Ser Phe Ala Glu Asp Ala Ser Ser
    45                  50                  55

AGT CTT AGA GCT TTG GGC TCA ACA AGG GCT TTC ACT TGC CAT TGC AGA      243
```

-continued

```
Ser Leu Arg Ala Leu Gly Ser Thr Arg Ala Phe Thr Cys His Cys Arg
 60                 65                  70                  75

AGG TCC TGT TAT TCA ACA GAA TAT TCC TAT GGG ACC TGC ACT GTC ATG      291
Arg Ser Cys Tyr Ser Thr Glu Tyr Ser Tyr Gly Thr Cys Thr Val Met
                 80                  85                  90

GGT ATT AAC CAC AGA TTC TGC TGC CTC TGAGGGATGA GAACAGAGAG            338
Gly Ile Asn His Arg Phe Cys Cys Leu  *
             95                 100

AAATATATTC ATAATTTACT TTATGACCTA GAAGGAAACT GTCGTGTGTC CCATACATTG    398

CCATCAACTT TGTTTCCTCA TCTCAAATAA AGTCCTTTCA GCAAAAAAAA AAAA          452
```

( 2 ) INFORMATION FOR SEQ ID NO:7:

( i ) SEQUENCE CHARACTERISTICS:
( A ) LENGTH: 100 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Arg Thr Leu Thr Ile Leu Thr Ala Val Leu Leu Val Ala Leu Gln
  1               5                  10                  15

Ala Lys Ala Glu Pro Leu Gln Ala Glu Asp Asp Pro Leu Gln Ala Lys
             20                  25                  30

Ala Tyr Glu Ala Asp Ala Gln Glu Gln Arg Gly Ala Asn Asp Gln Asp
         35                  40                  45

Phe Ala Val Ser Phe Ala Glu Asp Ala Ser Ser Ser Leu Arg Ala Leu
     50                  55                  60

Gly Ser Thr Arg Ala Phe Thr Cys His Cys Arg Arg Ser Cys Tyr Ser
 65                  70                  75                  80

Thr Glu Tyr Ser Tyr Gly Thr Cys Thr Val Met Gly Ile Asn His Arg
                 85                  90                  95

Phe Cys Cys Leu
            100
```

( 2 ) INFORMATION FOR SEQ ID NO:8:

( i ) SEQUENCE CHARACTERISTICS:
( A ) LENGTH: 202 base pairs
( B ) TYPE: nucleic acid
( C ) STRANDEDNESS: double
( D ) TOPOLOGY: unknown ( x i ) SEQUENCE DESCRIPTION: SEQ ID NO:8:

```
GAGGCCTGGG TCAGAGGACT TCTGTCTGCC CTTCTCTGCT CATCCCGCAT AGCCTGAGGA     60

TCTGTGCCTC CCAGCCATGA GGACCCTCGC TCTGCTTGCT GCCATTCTCC TGGTGGCCCT    120

GCAGGCCCAG GCTGAGCACA TTTCAGTGAG CATCGATGAA GTCGTAGACC AGCAGCCCCC    180

ACAGGCAGAG GATCAGGACG TG                                             202
```

( 2 ) INFORMATION FOR SEQ ID NO:9:

( i ) SEQUENCE CHARACTERISTICS:
( A ) LENGTH: 195 base pairs
( B ) TYPE: nucleic acid
( C ) STRANDEDNESS: double
( D ) TOPOLOGY: unknown ( x i ) SEQUENCE DESCRIPTION: SEQ ID NO:9:

```
GAGGCCTGGG TCAGAGGACT GCTGCCTGCC CCTCTCTGCT CATTCCATAC AGCCCTGTGC     60
```

-continued

```
CTCCCAGCCA TGAGGACCCT CGCTCTGCTT GCTGCCATTC TCCTGGTGGC CCTGCAGGCC    120

CAGGCTGAGC ACAGTTCAGT GAGCATCGAT GAAGTCGTAG ACCAGCAGCC CCCACAGGCA    180

GAGGATCAGG ACGTG                                                     195
```

( 2 ) INFORMATION FOR SEQ ID NO:10:

( i ) SEQUENCE CHARACTERISTICS:
( A ) LENGTH: 203 base pairs
( B ) TYPE: nucleic acid
( C ) STRANDEDNESS: double
( D ) TOPOLOGY: unknown ( x i ) SEQUENCE DESCRIPTION: SEQ ID NO:10:

```
AAGACCTGGG ACAGAGGACT GCTGTCTGCC CTCTCTGGTC ACCCTGCCTA GCTAGAGGAT     60

CTGTGACCCC AGCCATGAGG ACCCTCGCCA TCCTTGCTGC CATTCTCCTG GTGGCCCTGC    120

AGGCCCAGGC TGAGCCACTC CAGGCAAGAG CTGATGAGGT TGCTGCAGCC CCGGAGCAGA    180

TTGCAGCGGA CATCCCAGAA GTG                                            203
```

( 2 ) INFORMATION FOR SEQ ID NO:11:

( i ) SEQUENCE CHARACTERISTICS:
( A ) LENGTH: 203 base pairs
( B ) TYPE: nucleic acid
( C ) STRANDEDNESS: double
( D ) TOPOLOGY: unknown ( x i ) SEQUENCE DESCRIPTION: SEQ ID NO:11:

```
AAGACCTGGG ACAGAGGACT GCTGTCTGCC CTCTCTGGTC ACCCTGCCTA GCTAGAGGAT     60

CTGTGACCCC AGCCATGAGG ACCCTCGCCA TCCTTGCTGC CATTCTCCTG GTGGCCCTGC    120

AGGCCCAGGC TGAGCCACTC CAGGCAAGAG CTGATGAGGT TGCTGCAGCC CCGGAGCAGA    180

TTGCAGCGGA CATCCCAGAA GTG                                            203
```

( 2 ) INFORMATION FOR SEQ ID NO:12:

( i ) SEQUENCE CHARACTERISTICS:
( A ) LENGTH: 94 amino acids
( B ) TYPE: amino acid
( C ) STRANDEDNESS: single
( D ) TOPOLOGY: unknown ( x i ) SEQUENCE DESCRIPTION: SEQ ID NO:12:

```
Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Met Asn
    50                  55                  60

Ala Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90
```

( 2 ) INFORMATION FOR SEQ ID NO:13:

( i ) SEQUENCE CHARACTERISTICS:
( A ) LENGTH: 94 amino acids
( B ) TYPE: amino acid
( C ) STRANDEDNESS: single ( D ) TOPOLOGY: unknown ( x i ) SEQUENCE DESCRIPTION: SEQ ID NO:13:

Met Arg Thr Leu Ala Ile Leu Ala Ala Ile Leu Leu Val Ala Leu Gln
1 5 10 15

Ala Gln Ala Glu Pro Leu Gln Ala Arg Ala Asp Glu Val Ala Ala Ala
20 25 30

Pro Glu Gln Ile Ala Ala Asp Ile Pro Glu Val Val Val Ser Leu Ala
35 40 45

Trp Asp Glu Ser Leu Ala Pro Lys His Pro Gly Ser Arg Lys Met Asn
50 55 60

Asp Cys Tyr Cys Arg Ile Pro Ala Cys Ile Ala Gly Glu Arg Arg Tyr
65 70 75 80

Gly Thr Cys Ile Tyr Gln Gly Arg Leu Trp Ala Phe Cys Cys
85 90

( 2 ) INFORMATION FOR SEQ ID NO:14:

( i ) SEQUENCE CHARACTERISTICS:
( A ) LENGTH: 95 amino acids
( B ) TYPE: amino acid
( C ) STRANDEDNESS: single
( D ) TOPOLOGY: unknown ( x i ) SEQUENCE DESCRIPTION: SEQ ID NO:14:

Met Arg Thr Leu Ala Leu Leu Ala Ala Ile Leu Leu Val Ala Leu Gln
1 5 10 15

Ala Gln Ala Glu His Val Ser Val Ser Ile Asp Glu Val Val Asp Gln
20 25 30

Gln Pro Pro Gln Ala Glu Asp Gln Asp Val Ala Ile Tyr Val Lys Glu
35 40 45

His Glu Ser Ser Ala Leu Glu Ala Leu Gly Val Lys Ala Gly Val Val
50 55 60

Cys Ala Cys Arg Arg Ala Leu Cys Leu Pro Arg Glu Arg Arg Ala Gly
65 70 75 80

Arg Cys Arg Ile Arg Gly Arg Ile His Pro Leu Cys Cys Arg Arg
85 90 95

( 2 ) INFORMATION FOR SEQ ID NO:15:

( i ) SEQUENCE CHARACTERISTICS:
( A ) LENGTH: 95 amino acids
( B ) TYPE: amino acid
( C ) STRANDEDNESS: single
( D ) TOPOLOGY: unknown ( x i ) SEQUENCE DESCRIPTION: SEQ ID NO:15:

Met Arg Thr Leu Ala Leu Leu Ala Ala Ile Leu Leu Val Ala Leu Gln
1 5 10 15

Ala Gln Ala Glu His Ile Ser Val Ser Ile Asp Glu Val Val Asp Gln
20 25 30

Gln Pro Pro Gln Ala Glu Asp Gln Asp Val Ala Ile Tyr Val Lys Glu
35 40 45

His Glu Ser Ser Ala Leu Glu Ala Leu Gly Val Lys Ala Gly Val Val
50 55 60

Cys Ala Cys Arg Arg Ala Leu Cys Leu Pro Leu Glu Arg Arg Ala Gly
65 70 75 80

Arg Cys Arg Ile Arg Gly Arg Ile His Pro Leu Cys Cys Arg Arg
85 90 95

-continued ( 2 ) INFORMATION FOR SEQ ID NO:16:

( i ) SEQUENCE CHARACTERISTICS:
( A ) LENGTH: 93 amino acids
( B ) TYPE: amino acid
( C ) STRANDEDNESS: single
( D ) TOPOLOGY: unknown ( x i ) SEQUENCE DESCRIPTION: SEQ ID NO:16:

Met Lys Lys Leu Val Leu Leu Phe Ala Leu Val Leu Leu Gly Phe Gln
1 5 10 15

Val Gln Ala Asp Ser Ile Gln Asn Thr Asp Glu Glu Thr Lys Thr Glu
20 25 30

Glu Gln Pro Gly Glu Glu Asp Gln Ala Val Ser Val Ser Phe Gly Asp
35 40 45

Pro Glu Gly Thr Ser Leu Gln Glu Glu Ser Leu Arg Asp Leu Val Cys
50 55 60

Tyr Cys Arg Ser Arg Gly Cys Lys Gly Arg Glu Arg Met Asn Gly Thr
65 70 75 80

Cys Arg Lys Gly His Leu Leu Tyr Thr Leu Cys Cys Arg
85 90

( 2 ) INFORMATION FOR SEQ ID NO:17:

( i ) SEQUENCE CHARACTERISTICS:
( A ) LENGTH: 100 amino acids
( B ) TYPE: amino acid
( C ) STRANDEDNESS: single
( D ) TOPOLOGY: unknown ( x i ) SEQUENCE DESCRIPTION: SEQ ID NO:17:

Met Arg Thr Leu Ala Xaa Leu Ala Ala Ile Leu Leu Val Ala Leu Gln
1 5 10 15

Ala Gln Ala Glu Xaa Xaa Gln Xaa Xaa Xaa Asp Glu Xaa Xaa Xaa Xaa
20 25 30

Xaa Xaa Gln Xaa Xaa Glu Xaa Xaa Gln Val Xaa Xaa Ser Xaa Xaa Xaa
35 40 45

Xaa Xaa Xaa Xaa Xaa Ser Xaa Xaa Xaa Xaa Xaa Xaa Xaa Xaa Xaa Xaa
50 55 60

Xaa Xaa Xaa Xaa Xaa Xaa Cys Xaa Cys Arg Xaa Xaa Xaa Cys Xaa Xaa
65 70 75 80

Xaa Glu Arg Xaa Xaa Gly Xaa Cys Xaa Xaa Gly Xaa Xaa Xaa Xaa Xaa
85 90 95

Xaa Cys Cys Xaa
100

( 2 ) INFORMATION FOR SEQ ID NO:18:

( i ) SEQUENCE CHARACTERISTICS:
( A ) LENGTH: 30 amino acids
( B ) TYPE: amino acid
( C ) STRANDEDNESS: single
( D ) TOPOLOGY: unknown ( x i ) SEQUENCE DESCRIPTION: SEQ ID NO:18:

Ala Cys Tyr Cys Arg Ile Pro Ala Cys Ile Ala Gly Glu Arg Arg Tyr
1 5 10 15

Gly Thr Cys Ile Tyr Gln Gly Arg Leu Trp Ala Phe Cys Cys
20 25 30

( 2 ) INFORMATION FOR SEQ ID NO:19:

( i ) SEQUENCE CHARACTERISTICS:
( A ) LENGTH: 29 amino acids
( B ) TYPE: amino acid
( C ) STRANDEDNESS: single
( D ) TOPOLOGY: unknown ( x i ) SEQUENCE DESCRIPTION: SEQ ID NO:19:

Cys Tyr Cys Arg Ile Pro Ala Cys Ile Ala Gly Glu Arg Arg Tyr Gly
1 5 10 15

Thr Cys Ile Tyr Gln Gly Arg Leu Trp Ala Phe Cys Cys
20 25

( 2 ) INFORMATION FOR SEQ ID NO:20:

( i ) SEQUENCE CHARACTERISTICS:
( A ) LENGTH: 30 amino acids
( B ) TYPE: amino acid
( C ) STRANDEDNESS: single
( D ) TOPOLOGY: unknown ( x i ) SEQUENCE DESCRIPTION: SEQ ID NO:20:

Asp Cys Tyr Cys Arg Ile Pro Ala Cys Ile Ala Gly Glu Arg Arg Tyr
1 5 10 15

Gly Thr Cys Ile Tyr Gln Gly Arg Leu Trp Ala Phe Cys Cys
20 25 30

( 2 ) INFORMATION FOR SEQ ID NO:21:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:21:

Tyr Cys Ser Cys Arg Leu Val Phe Cys Arg Arg Thr Glu Leu Arg Val
1 5 10 15

Gly Asn Cys Leu Ile Gly Gly Val Ser Phe Thr Tyr Cys Cys Thr Arg
20 25 30

Val ( 2 ) INFORMATION FOR SEQ ID NO:22:

( i ) SEQUENCE CHARACTERISTICS:
( A ) LENGTH: 32 amino acids
( B ) TYPE: amino acid
( C ) STRANDEDNESS: single
( D ) TOPOLOGY: unknown ( x i ) SEQUENCE DESCRIPTION: SEQ ID NO:22:

Ala Thr Cys Tyr Cys Arg Thr Gly Arg Cys Ala Thr Arg Glu Ser Leu
1 5 10 15

Ser Gly Val Cys Glu Ile Ser Gly Arg Leu Tyr Arg Leu Cys Cys Arg
20 25 30

( 2 ) INFORMATION FOR SEQ ID NO:23:

( i ) SEQUENCE CHARACTERISTICS:
( A ) LENGTH: 31 amino acids
( B ) TYPE: amino acid
( C ) STRANDEDNESS: single
( D ) TOPOLOGY: unknown ( x i ) SEQUENCE DESCRIPTION: SEQ ID NO:23:

Val Cys Tyr Cys Arg Ser Arg Gly Cys Lys Gly Arg Glu Arg Met Asn

-continued 1 5 10 15

Gly Thr Cys Arg Lys Gly His Leu Leu Tyr Thr Leu Cys Cys Arg
20 25 30

( 2 ) INFORMATION FOR SEQ ID NO:24:

( i ) SEQUENCE CHARACTERISTICS:
( A ) LENGTH: 31 amino acids
( B ) TYPE: amino acid
( C ) STRANDEDNESS: single
( D ) TOPOLOGY: unknown ( x i ) SEQUENCE DESCRIPTION: SEQ ID NO:24:

Arg Arg Cys Ile Cys Thr Thr Arg Thr Cys Arg Phe Pro Tyr Arg Arg
1 5 10 15

Leu Gly Thr Cys Ile Phe Gln Asn Arg Val Tyr Thr Phe Cys Cys
20 25 30

( 2 ) INFORMATION FOR SEQ ID NO:25:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:25:

Val Val Cys Ala Cys Arg Arg Ala Leu Cys Leu Pro Arg Glu Arg Arg
1 5 10 15

Ala Gly Phe Cys Arg Ile Arg Gly Arg Ile His Pro Leu Cys Cys Arg
20 25 30

Arg ( 2 ) INFORMATION FOR SEQ ID NO:26:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:26:

Val Val Cys Ala Cys Arg Arg Ala Leu Cys Leu Pro Leu Glu Arg Arg
1 5 10 15

Ala Gly Phe Cys Arg Ile Arg Gly Arg Ile His Pro Leu Cys Cys Arg
20 25 30

Arg ( 2 ) INFORMATION FOR SEQ ID NO:27:

( i ) SEQUENCE CHARACTERISTICS:
( A ) LENGTH: 34 amino acids
( B ) TYPE: amino acid
( C ) STRANDEDNESS: single
( D ) TOPOLOGY: unknown ( x i ) SEQUENCE DESCRIPTION: SEQ ID NO:27:

Gly Ile Cys Ala Cys Arg Arg Arg Phe Cys Pro Asn Ser Glu Arg Phe
1 5 10 15

Ser Gly Tyr Cys Arg Val Asn Gly Ala Arg Tyr Val Arg Cys Cys Ser
20 25 30

Arg Arg

-continued ( 2 ) INFORMATION FOR SEQ ID NO:28:

( i ) SEQUENCE CHARACTERISTICS:
( A ) LENGTH: 34 amino acids
( B ) TYPE: amino acid
( C ) STRANDEDNESS: single
( D ) TOPOLOGY: unknown ( x i ) SEQUENCE DESCRIPTION: SEQ ID NO:28:

Gly Arg Cys Val Cys Arg Lys Gln Leu Leu Cys Ser Tyr Arg Glu Arg
1 5 10 15

Arg Ile Gly Asp Cys Lys Ile Arg Gly Val Arg Phe Pro Phe Cys Cys
20 25 30

Pro Arg ( 2 ) INFORMATION FOR SEQ ID NO:29:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:29:

Val Ser Cys Thr Cys Arg Arg Phe Ser Cys Gly Phe Gly Glu Arg Ala
1 5 10 15

Ser Gly Ser Cys Thr Val Asn Gly Val Arg His Thr Leu Cys Cys Arg
20 25 30

Arg ( 2 ) INFORMATION FOR SEQ ID NO:30:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:30:

Val Phe Cys Thr Cys Arg Gly Phe Leu Cys Gly Ser Gly Glu Arg Ala
1 5 10 15

Ser Gly Ser Cys Thr Ile Asn Gly Val Arg His Thr Leu Cys Cys Arg
20 25 30

Arg ( 2 ) INFORMATION FOR SEQ ID NO:31:

( i ) SEQUENCE CHARACTERISTICS:
( A ) LENGTH: 32 amino acids
( B ) TYPE: amino acid
( C ) STRANDEDNESS: single
( D ) TOPOLOGY: unknown ( x i ) SEQUENCE DESCRIPTION: SEQ ID NO:31:

Val Thr Cys Tyr Cys Arg Arg Thr Arg Cys Gly Phe Arg Glu Arg Leu
1 5 10 15

Ser Gly Ala Cys Gly Tyr Arg Gly Arg Ile Tyr Arg Leu Cys Cys Arg
20 25 30

( 2 ) INFORMATION FOR SEQ ID NO:32:

( i ) SEQUENCE CHARACTERISTICS:
( A ) LENGTH: 29 amino acids
( B ) TYPE: amino acid
( C ) STRANDEDNESS: single ( D ) TOPOLOGY: unknown ( x i ) SEQUENCE DESCRIPTION: SEQ ID NO:32:

Cys Ser Cys Arg Thr Ser Ser Cys Arg Phe Gly Glu Arg Leu Ser Gly
1 5 10 15

Ala Cys Arg Leu Asn Gly Arg Ile Tyr Arg Leu Cys Cys
20 25

( 2 ) INFORMATION FOR SEQ ID NO:33:

( i ) SEQUENCE CHARACTERISTICS:
( A ) LENGTH: 31 amino acids
( B ) TYPE: amino acid
( C ) STRANDEDNESS: single
( D ) TOPOLOGY: unknown ( x i ) SEQUENCE DESCRIPTION: SEQ ID NO:33:

Ala Cys Tyr Cys Arg Ile Gly Ala Cys Val Ser Gly Glu Arg Leu Thr
1 5 10 15

Gly Ala Cys Gly Leu Asn Gly Arg Ile Tyr Arg Leu Cys Cys Arg
20 25 30

( 2 ) INFORMATION FOR SEQ ID NO:34:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( x i ) SEQUENCE DESCRIPTION: SEQ ID NO:34:

Xaa Xaa Cys Xaa Cys Arg Xaa Xaa Xaa Cys Xaa Xaa Xaa Glu Arg Xaa
1 5 10 15

Xaa Gly Xaa Cys Xaa Xaa Xaa Gly Xaa Xaa Xaa Xaa Xaa Cys Cys Xaa
20 25 30

Xaa ( 2 ) INFORMATION FOR SEQ ID NO:35:

( i ) SEQUENCE CHARACTERISTICS:
( A ) LENGTH: 43 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:35:

CTTGCTGCCA TTCTCCTGGT GGCCCTGCAG GCCCAGGCTG AGC 43

( 2 ) INFORMATION FOR SEQ ID NO:36:

( i ) SEQUENCE CHARACTERISTICS:
( A ) LENGTH: 21 base pairs
( B ) TYPE: nucleic acid
( C ) STRANDEDNESS: single
( D ) TOPOLOGY: unknown ( x i ) SEQUENCE DESCRIPTION: SEQ ID NO:36:

GAGACCCGTA AGACGACGAC T 21

( 2 ) INFORMATION FOR SEQ ID NO:37:

( i ) SEQUENCE CHARACTERISTICS:
( A ) LENGTH: 24 base pairs
( B ) TYPE: nucleic acid -continued ( C ) STRANDEDNESS: single
( D ) TOPOLOGY: unknown ( x i ) SEQUENCE DESCRIPTION: SEQ ID NO:37:

TTCCCTGTAG CTCTCAAAGC AAAT 24

( 2 ) INFORMATION FOR SEQ ID NO:38:

( i ) SEQUENCE CHARACTERISTICS:
( A ) LENGTH: 218 base pairs
( B ) TYPE: nucleic acid
( C ) STRANDEDNESS: single
( D ) TOPOLOGY: unknown ( x i ) SEQUENCE DESCRIPTION: SEQ ID NO:38:

CCCTGCCTAG CTAGAGGATC TGTGACCCCA GCCATGAGGA CCCTCGCCAT CCTTGCTGCC 60

ATTCTCCTGG TGGCCCTGCA GGCCCAGGCT GAGCCACTCC AGGCAAGAGC TGATGAGGTT 120

GCTGCAGCCC CGGAGCAGAT TGCAGCGGAC ATCCCAGAAG TGGTTGTTTC CCTTGCATGG 180

GACGAAAGCT TGGCTCCAAA GCATCCAGGC TCAAGGAA 218

( 2 ) INFORMATION FOR SEQ ID NO:39:

( i ) SEQUENCE CHARACTERISTICS:
( A ) LENGTH: 20 base pairs
( B ) TYPE: nucleic acid
( C ) STRANDEDNESS: single
( D ) TOPOLOGY: unknown ( x i ) SEQUENCE DESCRIPTION: SEQ ID NO:39:

CGGCCACTGA TTTCACACAC 20

( 2 ) INFORMATION FOR SEQ ID NO:40:

( i ) SEQUENCE CHARACTERISTICS:
( A ) LENGTH: 21 base pairs
( B ) TYPE: nucleic acid
( C ) STRANDEDNESS: single
( D ) TOPOLOGY: unknown ( x i ) SEQUENCE DESCRIPTION: SEQ ID NO:40:

GATTGGCAAT GCCTGCTGGG A 21

( 2 ) INFORMATION FOR SEQ ID NO:41:

( i ) SEQUENCE CHARACTERISTICS:
( A ) LENGTH: 48 base pairs
( B ) TYPE: nucleic acid
( C ) STRANDEDNESS: single
( D ) TOPOLOGY: unknown ( x i ) SEQUENCE DESCRIPTION: SEQ ID NO:41:

GAGTGGCTCA GCCTGGGCCT GCAGGGCCAC CAGGAGAATG GCAGCAAG 48

( 2 ) INFORMATION FOR SEQ ID NO:42:

( i ) SEQUENCE CHARACTERISTICS:
( A ) LENGTH: 21 base pairs
( B ) TYPE: nucleic acid
( C ) STRANDEDNESS: single
( D ) TOPOLOGY: unknown ( x i ) SEQUENCE DESCRIPTION: SEQ ID NO:42:

CAGGTTGGTC TGGAATTCTG T 21

( 2 ) INFORMATION FOR SEQ ID NO:43:

-continued ( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( x i ) SEQUENCE DESCRIPTION: SEQ ID NO:43:

TACGACTCAC TATAGTTTTT TTTTTTTTTT 30

( 2 ) INFORMATION FOR SEQ ID NO:44:

( i ) SEQUENCE CHARACTERISTICS:
( A ) LENGTH: 17 base pairs
( B ) TYPE: nucleic acid
( C ) STRANDEDNESS: single
( D ) TOPOLOGY: unknown ( x i ) SEQUENCE DESCRIPTION: SEQ ID NO:44:

AATACGACTC ACTATAG 17

( 2 ) INFORMATION FOR SEQ ID NO:45:

( i ) SEQUENCE CHARACTERISTICS:
( A ) LENGTH: 20 base pairs
( B ) TYPE: nucleic acid
( C ) STRANDEDNESS: single
( D ) TOPOLOGY: unknown ( x i ) SEQUENCE DESCRIPTION: SEQ ID NO:45:

GGACTCACGG GTAGCACAAC 20

( 2 ) INFORMATION FOR SEQ ID NO:46:

( i ) SEQUENCE CHARACTERISTICS:
( A ) LENGTH: 48 base pairs
( B ) TYPE: nucleic acid
( C ) STRANDEDNESS: single
( D ) TOPOLOGY: unknown ( x i ) SEQUENCE DESCRIPTION: SEQ ID NO:46:

CTCTACAGAC TCTGCTGTCG CTGAGCTTCC TAGATAGAAA CCAAAGCA 48

( 2 ) INFORMATION FOR SEQ ID NO:47:

( i ) SEQUENCE CHARACTERISTICS:
( A ) LENGTH: 48 base pairs
( B ) TYPE: nucleic acid
( C ) STRANDEDNESS: single
( D ) TOPOLOGY: unknown ( x i ) SEQUENCE DESCRIPTION: SEQ ID NO:47:

TGCTTTGGTT TCTATCTAGG AAGCTCAGCG ACAGCAGAGT CTGTAGAG 48

( 2 ) INFORMATION FOR SEQ ID NO:48:

( i ) SEQUENCE CHARACTERISTICS:
( A ) LENGTH: 20 base pairs
( B ) TYPE: nucleic acid
( C ) STRANDEDNESS: single
( D ) TOPOLOGY: unknown ( x i ) SEQUENCE DESCRIPTION: SEQ ID NO:48:

TCGCCATCCT TGCTGCCATT 20

( 2 ) INFORMATION FOR SEQ ID NO:49:

( i ) SEQUENCE CHARACTERISTICS:

-continued ( A ) LENGTH: 21 base pairs
( B ) TYPE: nucleic acid
( C ) STRANDEDNESS: single
( D ) TOPOLOGY: unknown ( x i ) SEQUENCE DESCRIPTION: SEQ ID NO:49:

CCCTGCCTAG CTAGAGGATT T 21

( 2 ) INFORMATION FOR SEQ ID NO:50:

( i ) SEQUENCE CHARACTERISTICS:
( A ) LENGTH: 43 base pairs
( B ) TYPE: nucleic acid
( C ) STRANDEDNESS: single
( D ) TOPOLOGY: unknown ( x i ) SEQUENCE DESCRIPTION: SEQ ID NO:50:

CTCACTGCTG TTCTCCTCGT GGCCCTCCAG GCCAAGGCTG AGC 43

( 2 ) INFORMATION FOR SEQ ID NO:51:

( i ) SEQUENCE CHARACTERISTICS:
( A ) LENGTH: 30 amino acids
( B ) TYPE: amino acid
( C ) STRANDEDNESS: single
( D ) TOPOLOGY: unknown ( x i ) SEQUENCE DESCRIPTION: SEQ ID NO:51:

```
Thr Cys His Cys Arg Arg Ser Cys Tyr Ser Thr Glu Tyr Ser Tyr Gly
 1               5                  10                  15

Thr Cys Thr Val Met Gly Ile Asn His Arg Phe Cys Cys Leu
            20                  25                  30
```